US008326404B2

(12) United States Patent
Zeng et al.

(10) Patent No.: US 8,326,404 B2
(45) Date of Patent: Dec. 4, 2012

(54) MULTIMODAL DETECTION OF TISSUE ABNORMALITIES BASED ON RAMAN AND BACKGROUND FLUORESCENCE SPECTROSCOPY

(75) Inventors: Haishan Zeng, Vancouver (CA); Harvey Lui, Singapore (SG); Zhiwei Huang, Singapore (SG); David I. McLean, Vancouver (CA)

(73) Assignee: British Columbia Cancer Agency Branch, Vancouver (CA)

( * ) Notice: Subject to any disclaimer, the term of this patent is extended or adjusted under 35 U.S.C. 154(b) by 1081 days.

(21) Appl. No.: 10/596,072

(22) PCT Filed: Nov. 26, 2004

(86) PCT No.: PCT/CA2004/002040
§ 371 (c)(1),
(2), (4) Date: May 12, 2008

(87) PCT Pub. No.: WO2005/052558
PCT Pub. Date: Jun. 9, 2005

(65) Prior Publication Data
US 2008/0221457 A1    Sep. 11, 2008

Related U.S. Application Data

(60) Provisional application No. 60/525,139, filed on Nov. 28, 2003.

(51) Int. Cl.
*A61B 6/00* (2006.01)
(52) U.S. Cl. ........................................ 600/475; 600/477
(58) Field of Classification Search .................. 600/473, 600/476
See application file for complete search history.

(56) References Cited

U.S. PATENT DOCUMENTS

| | | | |
|---|---|---|---|
| 4,832,483 A | 5/1989 | Verma |
| 5,131,398 A | 7/1992 | Alfano et al. |
| 5,261,410 A | 11/1993 | Alfano et al. |
| 5,293,872 A | 3/1994 | Alfano et al. |
| 5,369,496 A | 11/1994 | Alfano et al. |
| 5,450,857 A | 9/1995 | Garfield et al. |
| 5,596,992 A | 1/1997 | Haaland et al. |
| 5,612,540 A | 3/1997 | Richards-Kortum et al. |
| 5,697,373 A | 12/1997 | Richards-Kortum et al. |
| 5,769,081 A | 6/1998 | Alfano et al. |
| 5,991,653 A | 11/1999 | Richards-Kortum et al. |
| 6,008,889 A | 12/1999 | Zeng et al. |
| 6,069,689 A | 5/2000 | Zeng et al. |

(Continued)

FOREIGN PATENT DOCUMENTS

| | | |
|---|---|---|
| CA | 2322768 A1 | 9/1999 |
| CA | 2414289 A1 | 1/2002 |
| CA | 2429332 A1 | 5/2002 |

(Continued)

OTHER PUBLICATIONS

Song et al., Fluorescence and Raman spectroscopy, Gastrointest Endoscopy Clin, 13 (2003) 279-296.

(Continued)

*Primary Examiner* — Jacqueline Cheng
(74) *Attorney, Agent, or Firm* — Oyen Wiggs Green & Mutala LLP

(57) ABSTRACT

Methods and apparatus for classifying tissue use features of Raman spectra and background fluorescent spectra. The spectra may be acquired in the near-infrared wavelengths. Principal component analysis and linear discriminant analysis of reference spectra may be used to obtain a classification function that accepts features of the Raman and background fluorescence spectra for test tissue and yields an indication as to the likelihood that the test tissue is abnormal. The methods and apparatus may be applied to screening for skin cancers or other diseases.

34 Claims, 28 Drawing Sheets

U.S. PATENT DOCUMENTS

| | | |
|---|---|---|
| 6,095,982 A | 8/2000 | Richards-Kortum et al. |
| 6,135,965 A | 10/2000 | Tumer et al. |
| 6,174,291 B1 | 1/2001 | McMahon et al. |
| 6,205,354 B1 | 3/2001 | Gellermann et al. |
| 6,258,576 B1 | 7/2001 | Richards-Kortum et al. |
| 6,377,841 B1 | 4/2002 | Lin et al. |
| 6,385,484 B2 | 5/2002 | Nordstrom et al. |
| 6,485,413 B1 | 11/2002 | Boppart et al. |
| 6,697,652 B2 | 2/2004 | Georgakoudi et al. |
| 2003/0208169 A1 | 11/2003 | Chaiken et al. |
| 2003/0231309 A1 | 12/2003 | Fulghum, Jr. et al. |
| 2004/0004194 A1 | 1/2004 | Amblard et al. |
| 2004/0006276 A1 | 1/2004 | Demos et al. |
| 2004/0039269 A1 | 2/2004 | Ward et al. |
| 2004/0162489 A1 | 8/2004 | Richards-Kortum et al. |
| 2004/0253575 A1 | 12/2004 | Manfait et al. |

FOREIGN PATENT DOCUMENTS

| | | |
|---|---|---|
| WO | 0203857 A2 | 1/2002 |
| WO | 0207585 A2 | 1/2002 |
| WO | 03062798 A1 | 7/2003 |
| WO | 2004051242 A1 | 6/2004 |

OTHER PUBLICATIONS

Georgakoudi et al., The combined use of fluorescence, reflectance, and light-scattering spectroscopy for evaluating dysplasia in Barrett's esophagus, Gastrointest Endoscopy Clin N Am, 14 (2004) 519-537.

Sigurdsson et al., Detection of Skin Cancer by Classification of Raman Spectra, IEEE (2004), Transactions on Biomedical Engineering, No. 10, vol. 51.

Stone et al., Raman spectroscopy for identification of epithelial cancers, Faraday Discuss., 126 (2004) 141-157.

McLean et al., General Discussion, Faraday Discuss., 126 (2004) 169-183.

Lieber et al., Automated Method for Subtraction of Fluorescence from Biological Raman Spectra, Applied Spectroscopy, 57 (2003) No. 11, 1363-1367.

Yamazaki et al., The Diagnosis of Lung Cancer Using 1064-nm Excited Near-infrared Multichannel Raman Spectroscopy, Radiation Medicine, 21 (2003) No. 1, 1-6.

Hug, William et al.. "Portable Integrated UV Resonance Fluorescence and Raman Chemical Sensor for in situ, autonomous, detection." Emerging Technologies for Process Analysis. Oct. 5, 2004. FACSS. Oct. 12, 2004 <https://www.facss.ort/contentmgr/showdetails.php/id/23099>.

Gillies et al.. "Southwest Animal Imaging Resource." Southwest Animal Imaging Resource, University of Arizona. Mar. 6, 2002. The University of Arizona. Mar. 17, 2005 <http://www.swair.arizona.edu/index.html>.

MULTIMODAL DETECTION OF TISSUE ABNORMALITIES BASED ON RAMAN AND BACKGROUND FLUORESCENCE SPECTROSCOPY

CROSS REFERENCE TO RELATED APPLICATION

This application claims the benefit of application No. 60/525,139 filed on 28 Nov. 2003 which is hereby incorporated herein by reference in its entirety.

TECHNICAL FIELD

The invention relates to the detection of tissue abnormalities. The invention may be applied, for example, to screening subjects for tumors or other cancerous lesions. The invention may be applied to screening skin tissues or other tissues.

BACKGROUND

Skin cancer is the most common cancer in North America. Over 550,000 new cases of skin cancer are diagnosed each year. One in seven Canadians will develop a skin cancer during their lifetime. If detected early, skin cancer can be cured by relatively minor surgical removal. However, if detected late, more extensive and disfiguring surgery becomes necessary. It is especially important to diagnose malignant melanoma early. If treatment for malignant melanoma is commenced too late, systemic metastasis and death can occur.

At present, skin cancers are detected primarily by visual inspection by physicians. However, clinical accuracy of visual diagnoses is 75% at best. Definitive diagnosis is therefore based on histological examination of skin biopsy. Excisional biopsy currently remains the most reliable diagnostic approach for the early detection of skin cancer, but is invasive and impractical for screening high-risk patients who may have multiple suspicious lesions. Many unnecessary biopsies are done, at considerably cost to the health care system. Moreover, some needed biopsies may not be performed because of a failure to recognize a cancer.

During skin cancer treatment, visual assessment is also relied upon to determine the extent of the tumor, and therefore the amount of tissue to be either excised or irradiated. If a tumor has margins that are poorly defined, it may be necessary to perform repeated biopsy procedures from multiple sites in a time-consuming, expensive, and tedious procedure known as Mohs micrographic surgery.

Following skin cancer treatment, ongoing patient monitoring by visual inspection and periodic microscopic examination is required for detecting recurrent tumor or de novo skin cancer at other sites. All stages in the management of skin cancer would be facilitated by techniques that could provide accurate diagnostic information without requiring multiple expensive and potentially disfiguring skin biopsies.

A variety of approaches for noninvasive diagnosis of the skin have been developed using either optical or non-optical methods. Non-optical methods include ultrasound and MRI, while skin reflectance, autofluorescence, and thermography involve measurement of cutaneous optical properties that are altered in disease states. Many groups in the world are working to develop reflectance skin imaging methods (analogous to digital photography) for improving the early detection of skin cancer using digital processing. This approach has improved the registration, recording, and documentation of skin lesions, but has not yet significantly improved the accuracy of non-invasive diagnoses.

Raman spectroscopy and fluorescence spectroscopy have both been suggested as tools for the diagnosis of cancers. Raman spectroscopy measures the wavelength and intensity of light which has been scattered inelastically from molecular systems. Raman scattered light has wavelengths that are shifted from that of the incident light by amounts corresponding to the energies of excitations of the molecular systems. The excitations are typically vibrations.

Raman scattered light is typically relatively faint. When monochromatic light strikes a sample, almost all the observed light is scattered elastically (Rayleigh scattering) with no change in energy (or wavelength). Only a very small portion of the scattered light, typically approximately 1 part in $10^8$, is inelastically scattered (Raman scattering). Raman peaks are typically narrow and in many cases can be attributed to the vibration of specific chemical bonds (or normal modes dominated by the vibration of a functional group) in a molecule. As such, a Raman spectrum provides a "fingerprint" for the presence of various molecular species. Raman spectroscopy can be used for both qualitative identification and quantitative determination of molecular species.

Raman spectra have been observed from various biological tissues including skin. Identified Raman scatterers in tissues include elastin, collagen, blood, lipid, tryptophan, tyrosine, carotenoid, myoglobin, nucleic acids etc. Raman spectroscopy has also been used to monitor cutaneous drug delivery and pharmacokinetics during skin disease treatment. It has been used to monitor blood analytes, e.g. glucose, lactic acid, and urea, in blood samples.

Most studies which have investigated the Raman spectra of tissues have investigated ex vivo tissue samples using Fourier-Transform (FT) Raman spectrometers. FT-Raman systems take up to ½ hour to acquire a spectrum and are bulky and not portable, and therefore are of limited clinical utility. Recently developed dispersive type Raman systems based on fiber optic light delivery and collection, compact diode lasers, and high efficiency spectrograph-detector combinations, have shortened the time required to obtain a Raman spectrum to minutes or sub-minutes.

In addition to scattering and reflecting light, tissues can also absorb light and emit the absorbed energy in the form of fluorescent light that is of a longer wavelength than the incident light. Such "autofluorescence" signals are weak but can be detected. Fluorescence excitation and emission studies of tissues are usually performed in the ultraviolet and visible wavelength ranges.

Recently, some tissue autofluorescence studies have been conducted at longer red to near infrared (NIR) wavelengths. Some examples are Zhang G, et al., *Far-red and NIR Spectral Wing Emission from Tissues under* 532 *and* 632 *nm Photoexcitation* Lasers in Life Science 9:1-16, 1999 and Demos S G, et al. *Tissue imaging for cancer detection using NIR autofluorescence*, Proceedings SPIE 4613:31-34, 2002.

A problem with the evaluation of pigmented lesions, including melanoma and its precursors, by reflectance or visible fluorescence techniques is that melanin is a strong light absorber throughout the ultraviolet and visible spectrum. Both incident and reflected or re-emitted (fluorescent) photons in this wavelength range are largely absorbed by melanin. This results in weak spectra and "black hole" images that provide little clinically useful information.

Richards-Kortum et al., U.S. Pat. No. 6,095,982; discloses the use of a combination of fluorescence and Raman spectroscopy in detecting pre-cancers and other abnormalities in tissue. The fluorescence measurements are made in the ultraviolet while the Raman spectroscopy measurements are made in the infrared. Richards-Kortum et al, U.S. Pat. Nos. 5,991, 653; 5,697,373; 5,612,540 and 6,258,576 disclose similar methods.

Verma U.S. Pat. No. 4,832,483 discloses a method for using Raman spectroscopy for the detection of cancers. Georgakoudi et al. U.S. Pat. No. 6,697,652 disclose a method for evaluating tissue using multiple spectroscopic techniques including fluorescence, reflectance and light scattering spectra. Nordstrom et al. U.S. Pat. No. 6,385,484 discloses the use of fluorescence spectra and reflectance spectra for classifying tissue specimens. Tumer et al. U.S. Pat. No. 6,135,965 discloses the use of neural networks to identify spectra corresponding to abnormal tissues.

Alfano et al. U.S. Pat. No. 5,293,872 relates to methods which include the use of Rarnan spectroscopy for distinguishing between calcified atherosclerotic tissue and fibrous atherosclerotic tissue. Alfano et al., U.S. Pat. No. 5,131,398 discloses a method which uses native fluorescence for distinguishing cancerous tissue from benign tumour tissue. Alfano et al., U.S. Pat. No. 5,261,410 discloses a method for using Raman spectroscopy for determining whether a tissue is a malignant tumour tissue, a benign tumour tissue or a normal tissue. Alfano et al., U.S. Pat. No. 5,369,496 discloses the use of back-scattered light for evaluating tissue samples.

Puppels et al., WO 2004/051242 discloses the use of high-wavenumber Raman spectroscopy for detecting abnormalities in tissue. Haaland et al., U.S. Pat. No. 5,596,992 discloses the use of multivariate classification techniques applied to infrared spectra from cell and tissue samples. Gellermann et al. U.S. Pat. No. 6,205,354 discloses the use of Raman spectroscopy for detection of carontenoids. Lin et al., U.S. Pat. No. 6,377,841 disclose the use of fluorescence and diffuse reflectance spectra for detecting the boundaries of brain tumours. Garfield et al., U.S. Pat. No. 5,450,857 discloses the use of fluorescence spectra for measuring cervical dilation. Boppart et al. U.S. Pat. No. 6,485,413 discloses a instrument which can be used for collecting various spectra including fluorescence spectra and Raman spectra.

Empirically determined diagnostic algorithms based on the determined peak intensities, widths, and/or peak ratios of tissue spectra have been described in literature for evaluating variations in tissue spectra with tissue pathology. Some examples are Mahadevan-Jansen A, and Richards-Kortum R. *Raman spectroscopy for the detection of cancers and precancers*, J Biomed Opt 1996; 1, 31-70; Mahadevan-Jansen A, et al. *Near-infrared Raman spectroscopy for in vitro detection of cervical precancers* Photochem Photobiol 1998; 68:123-132; and, Huang Z, et al., *Near-infrared Raman spectroscopy for optical diagnosis of lung cancer*, Int J Cancer, 2003; 107: 1047-1052.

Multivariate statistical techniques have been applied for similar purposes. Examples include: Bakker Schut TC et al. *In vivo detection of dysplastic tissue by Raman spectroscopy* Anal Chem 2000; 72:6010-6018; Mahadevan-Jansen A, et al. *Near-infrared Raman spectroscopy for in vitro detection of cervical precancers* Photochem Photobiol 1998; 68:123-132; Stone N, et al. *Near-infrared Raman spectroscopy for the classification of epithelial pre-cancers and cancers*, J Raman Spectrosc 2002; 33: 564-573; Deinum G, et al., *Histological classification of Raman spectra of human coronary artery atherosclerosis using principal component analysis*, Appl Spectrosc 1999; 53:938-942; and, Silveira L Jr et al., *Correlation between near-infrared Raman spectroscopy and histopathological analysis of atherosclerosis in human coronary arteries*, Lasers Surg Med 2002; 30:290-7.

To date, none of the diagnostic methods described in the publications listed above have been widely adopted for use in tissue screening.

Despite the large amount of research that has been done in the area, there remains a need for fast, accurate cost-effective methods and apparatus capable of screening for tumours or other cancerous lesions.

SUMMARY OF THE INVENTION

One aspect of this invention provides methods for characterizing tissues. The methods may provide an indication as to whether or not a section of tissue is likely abnormal. The methods comprise obtaining features of a Raman spectrum of the tissue in a first wavelength range; obtaining features of a background fluorescence spectrum of the tissue in a second wavelength range that overlaps with the first wavelength range and characterizing the tissue based upon at least the Raman spectrum features and the background fluorescence spectrum features. The characterization may be performed, for example, by applying a classification function or supplying the features of the Raman and background autofluorescence spectra to a neural network. Suitable classification functions may be derived, for example, by performing PCA (Principal Components analysis) and LDA (Linear Discriminant Analysis) on reference data.

Another aspect of the invention provides methods for determining melanin content of tissues. The methods comprise obtaining a NIR spectrum of the tissue, the spectrum including first and second peaks at wavenumbers of approximately 1368 $cm^{-1}$ and 1572 $cm^{-1}$; subtracting a background of the spectrum to yield a Raman spectrum; and computing the melanin content of the tissue based upon intensities of at least one of the first and second peaks of the Raman spectrum.

Further aspects of the invention and features of specific embodiments of the invention are described below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention provides methods for detecting abnormalities in tissues. Methods according to the invention illuminate a section of tissue under investigation and acquire a spectrum in a wavelength range which includes both Raman features and background fluorescence. Both the Raman features and background fluorescence are used as a basis for evaluating whether or not the section of tissue under investigation is likely to be abnormal. Specific embodiments of the invention may be applied to screening skin or other tissues, such as lung tissues, epithelial tissues, such as the lining of the digestive tract, tissues of internal organs, or other tissues for cancers. The methods of the invention may be applied to tissues in vivo. The methods may also be applied in vitro.

The section of tissue may be, for example:
- an area of skin of a subject,
- a section of a piece of tissue obtained from a biopsy or surgery,
- a section of lung or other tissue from which a spectrum can be obtained using an endoscopic instrument, or
- a section of tissue that has become exposed during surgery.

In some embodiments of the invention the wavelength range covers a portion of the spectrum in the near infrared (NIR). In some embodiments of the invention the wavelength range spans at least from about 800 nm to about 1000 nm.

Determining whether or not a spectrum from a section of tissue under investigation indicates that the tissue may be abnormal may involve statistical analysis comparing the measured spectrum to reference data. The reference data may include or be based upon reference spectra taken of tissues which are known to be normal and/or abnormal. The reference data may be taken from tissues which are known to be normal or abnormal on the basis of reliable diagnostic techniques such as histopathological diagnosis. The comparison of the measured spectrum to the reference data may involve applying a principal components analysis (PCA) and linear discriminant analysis (LDA) to the reference data as in the examples given below. In the alternative, or additionally, features from the Raman and background fluorescence spectra may be provided to a neural network which has been trained to identify and/or characterize abnormal tissue samples based at least in part on the features of the Raman and background fluorescence spectra.

Figure 15:
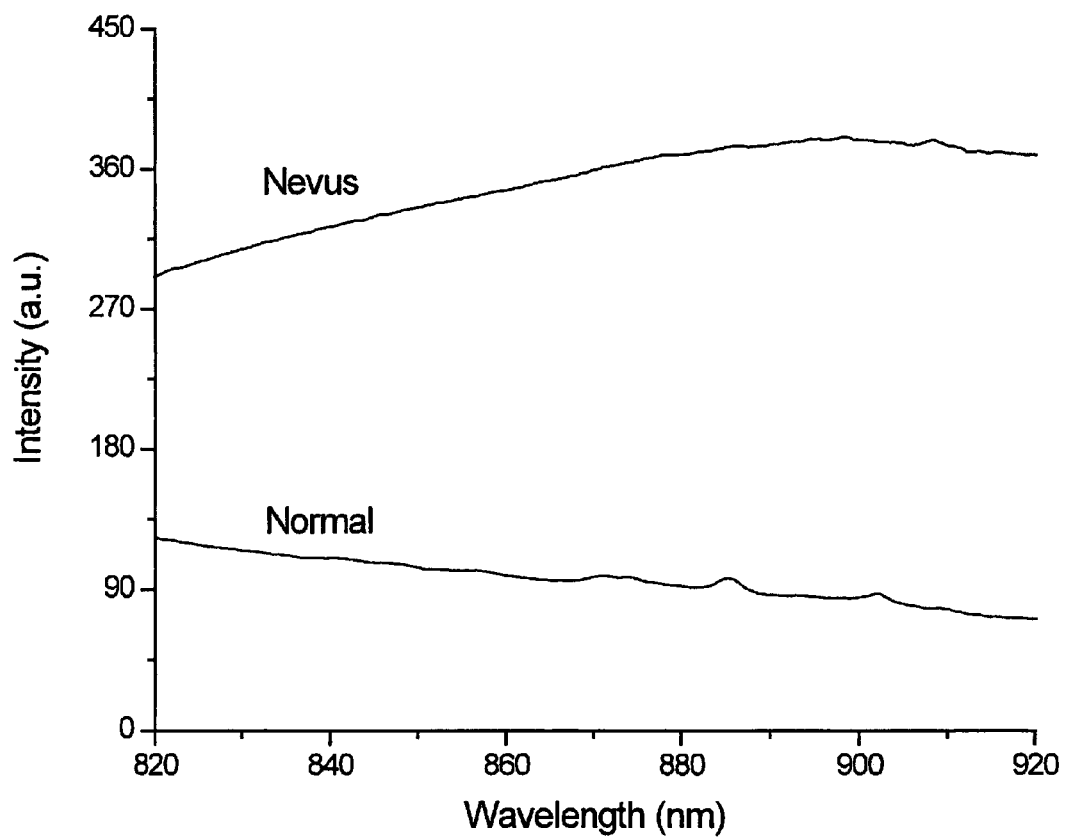
FIG. 15 compares NIR background fluorescence spectra for normal and nevus tissue.
Figure 15A:
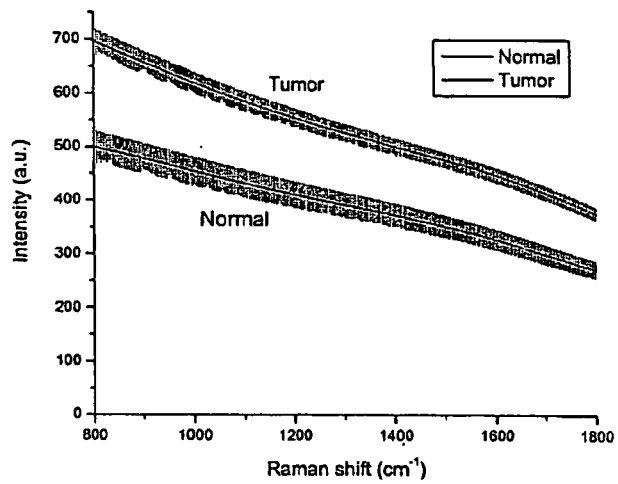
Figure 15B:
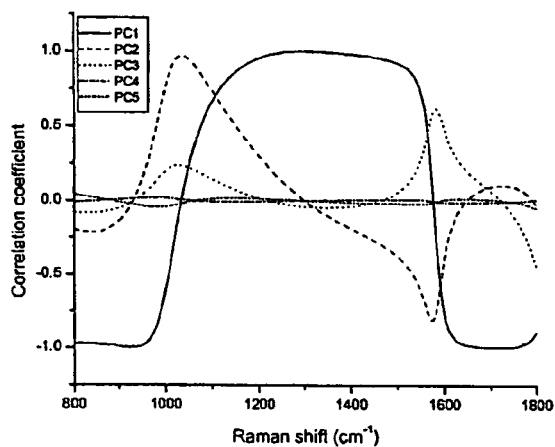
Figure 15C:
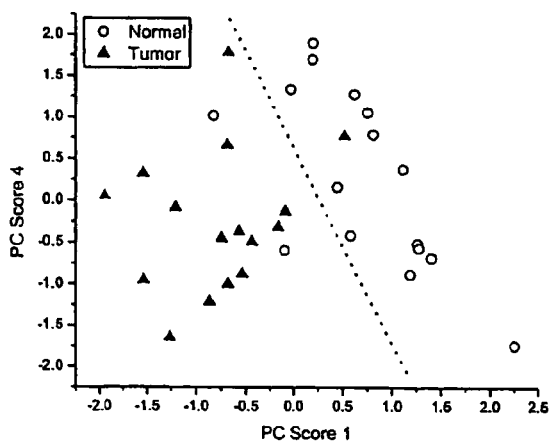
Figure 16:
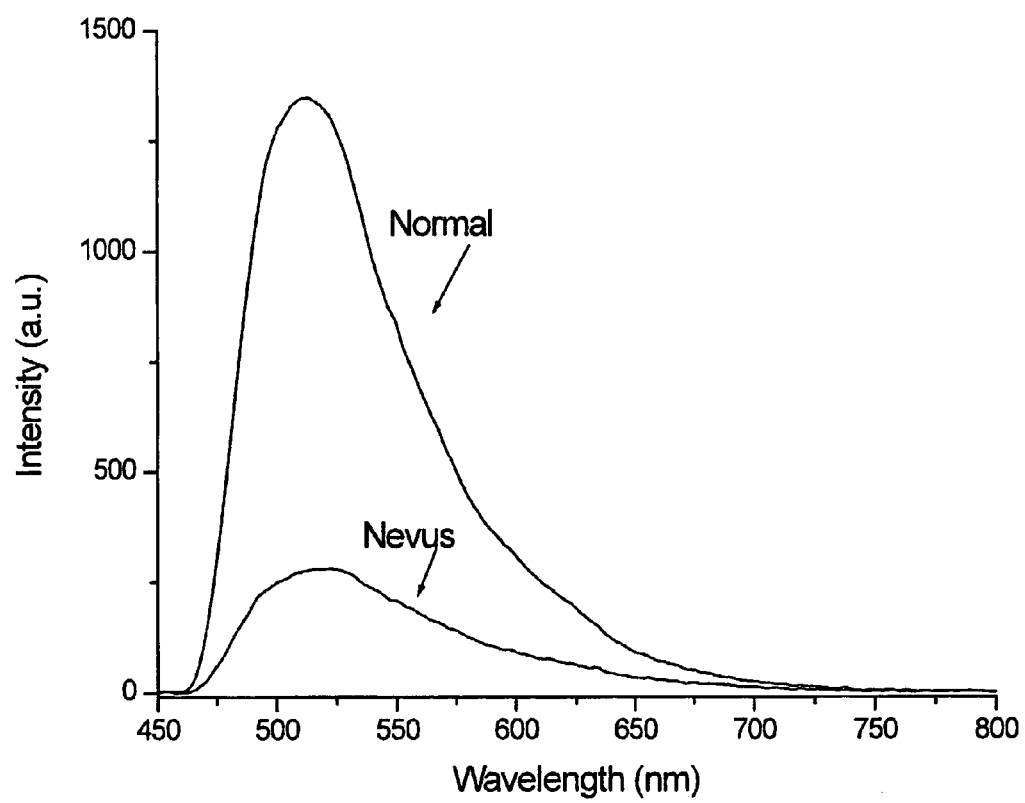
FIG. 16 compares visible fluorescence spectra for normal and nevus tissues.
Figure 16A:
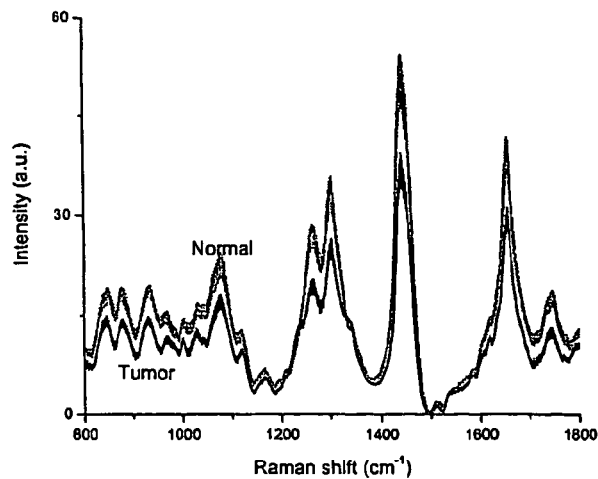
Figure 16B:
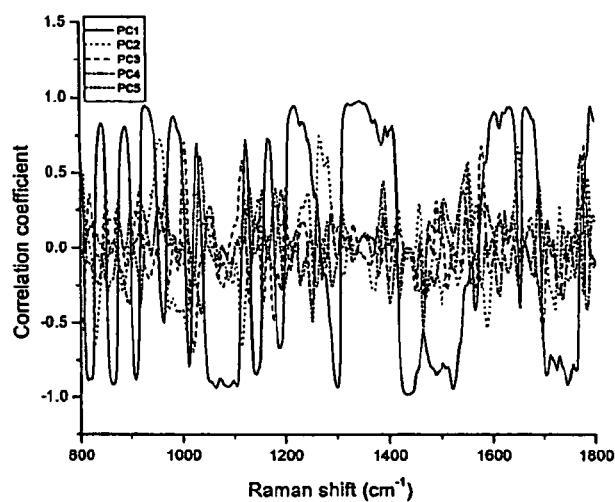
Figure 16C:
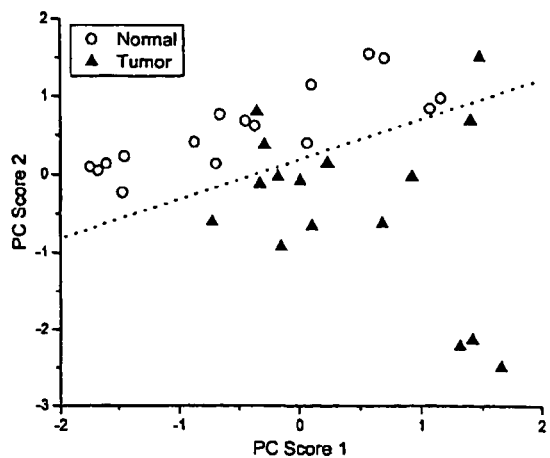

The inventors have observed that in vivo tissue NIR autofluorescence excited by 785 nm laser light exhibits trends different from shorter wavelength visible tissue autofluorescence between normal and diseased tissue. For example, skin affected by vitiligo has lower NIR fluorescence but higher visible fluorescence than surrounding normal skin, while skin affected by compound nevus has higher NIR fluorescence but lower visible fluorescence than surrounding normal skin (See FIGS. 15 and 16). A major difference between vitiligo and normal skin as well as between compound nevus and normal skin is the amount of melanin. Skin affected by melanoma also exhibits increased NIR autofluorescence as compared to surrounding normal skin. The inventors have also observed increased NIR autofluorescence emission in human skin squamous cell carcinoma. In contrast, skin basal cell carcinoma exhibits lower NIR autofluorescence emission than its surrounding normal skin. These differences in the NIR spectra between normal and abnormal tissues can be exploited in combination with features of Raman spectra of the tissues to characterise skin and other tissues.

Other modalities may optionally be combined with features from the Raman and background fluorescence spectra to improve the accuracy (e.g. the specificity and/or sensitivity) of the results obtained using Raman and background fluorescence spectra alone. For example, a melanin content of the section of tissue may be used as an additional feature. Raman spectroscopy may be used to measure the melanin content of a tissue, as described below. The additional modalities may include one or more modalities such as:
- UV or visible fluorescence spectra;
- diffuse reflectance spectra;
- light scattering spectra, which measure the scattering properties of tissue as a function of wavelength; and,
- differences between one or more Raman and/or NIR background autofluorescence features of a spectrum of the tissue being investigated and corresponding features of normal tissue of the same patient.

The inventors have discovered that for Raman and fluorescence spectra in the NIR, where the section of tissue is skin, the spectra of normal tissues depends upon the location on the subject's body of the section of tissue. For example, normal skin of the hands tends to exhibit similar spectral characteristics among different subjects. In contrast, NIR/Raman spectral characteristics of normal skin of the hands, head, arms and trunk, and thighs tend to be different from one another, even on the same subject. In some embodiments of the invention, classification functions are derived from reference spectra for the same body area as the body area in which the section of tissue under investigation is located. Some embodiments of the invention provide a plurality of classification functions each derived from a different set of reference data, each associated with a different body area. For example, a set of reference data may be provided for each of two or more of: the hands; the head; the arms and torso; and the thighs.

Apparatus

Any suitable apparatus may be used to acquire Raman and background fluorescence spectra of tissue in a desired wavelength range. Where the methods of the invention are to be used for in vivo screening it is generally desirable that the apparatus be capable of acquiring the Raman and background autofluorescence spectra reasonably quickly and that the apparatus not be unduly bulky.

Figure 1:
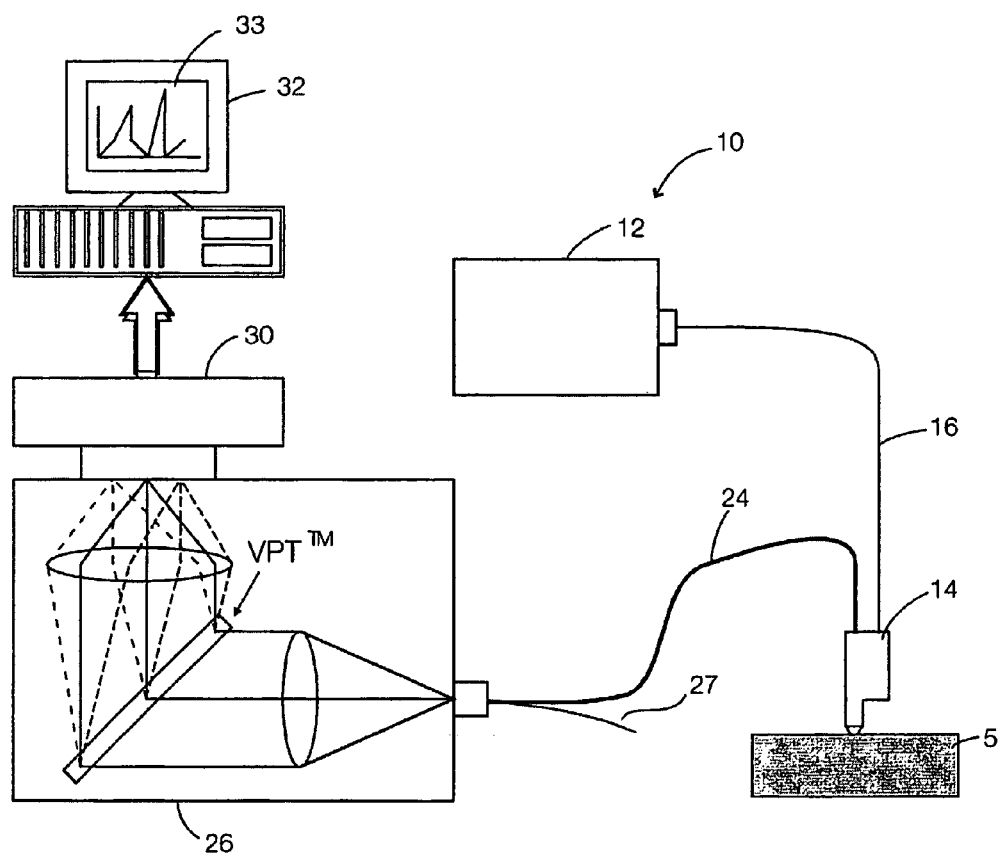
FIG. 1 is a block diagram of an apparatus that may be used for acquiring Raman and background fluorescence spectra.

FIG. 1 is a block diagram of apparatus 10 that may be used to acquire a Raman and background fluorescence spectrum. Apparatus 10 may be constructed as described in U.S. Pat. No. 6,486,948 and Huang Z. et al. *Rapid near-infrared Raman spectroscopy system for real-time in vivo skin measurements*, Opt Lett 2001; vol. 26: pp. 1782-1784 which are hereby incorporated herein by reference. Apparatus 10 includes a light source 12, typically a monochromatic light source, most typically a laser. In currently preferred embodiments of the invention, light source 12 emits light in the NIR (600 nm to 1200 nm). In an example embodiment, light source 12 is a laser diode that emits light having a wavelength of 785 nm. In a prototype embodiment of the invention, light source 12 is a 300 mW laser diode emitting light at 785 nm of the type available from SDL Inc. of San Jose, Calif.

Figure 1A:
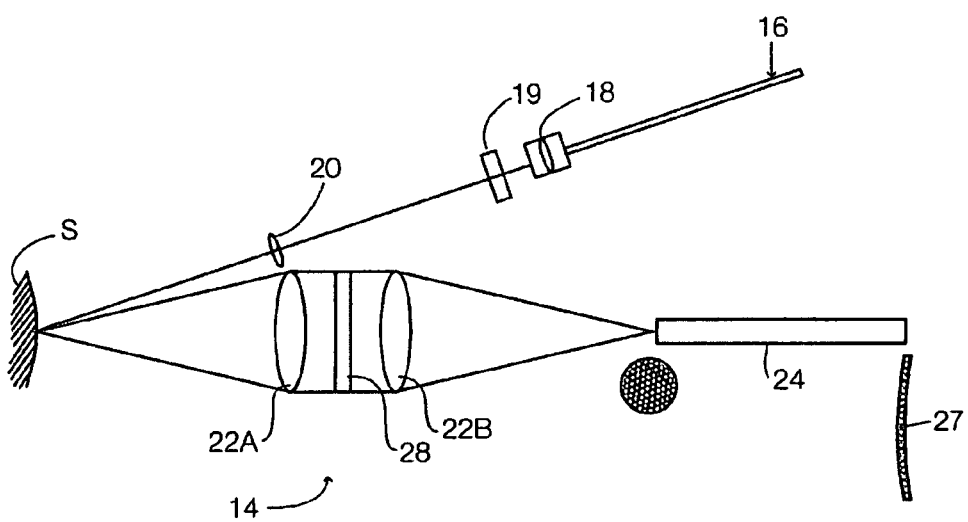
FIG. 1A is a schematic block diagram of the probe of the apparatus of FIG. 1.

Light from light source 12 is delivered to a probe 14 through an optical fiber 16. In the prototype, optical fiber 16 is a 200 µm core diameter fiber having a numerical aperture ("NA") of 0.22. As shown in FIG. 1A, probe 14 includes a collimator 18 and a bandpass filter 19 which ensures that light directed onto tissue S is essentially monochromatic. In the prototype, bandpass filter 19 has a passband of 785 nm±2.5 nm. A lens 20 focuses the monochromatic light onto tissue S. In the prototype, lens 20 provides a spot size of 3.5 mm. A shutter (not shown) may be mounted at the laser output port of laser 12. The shutter may be kept closed except during the acquisition of spectral data to ensure that the subject's skin is exposed to laser light only as necessary to acquire data.

Light which has been backscattered from tissue S is focused by lenses 22A, and 22B into a fiber optic bundle 24. A notch filter 28 blocks light which is outside of a wavelength range of interest. In the prototype, filter 28 is a holographic filter having optical density ("OD")>6.0 at 785 nm.

Fiber optic bundle 24 carries the backscattered light to a spectrometer 26. To enhance the detection sensitivity, the fiber optic bundle 24 used in the prototype includes as many fibers as could be imaged onto the light sensor of spectrometer 26. In the prototype bundle 24 has 58 100 µm fibers arranged at its input end at probe 14 in a circular shape having a diameter of 1.6 mm and arranged in a generally linear array at its output end at the entrance of spectrograph 26. The prototype had a 50 µm calibration fiber 27 located at the center of the output linear array. Light of a known wavelength can be delivered to spectrometer 26 by way of calibration fiber 27 for wavelength calibration of spectrometer 26.

In the prototype, spectrometer 26 is a HoloSpec™ f/2.2 NIR spectrometer equipped with a volume phase technology (VPT) holographic grating model HSG-785-LF available from Kaiser Optical Systems, Inc. of Ann Arbor, Mich. USA. Spectrometer 26 includes a light detector, such as a CCD camera 30. In the prototype, camera 30 is a 1024×256 pixel liquid-nitrogen-cooled, NIR-optimized, back-illuminated, deep-depletion, CCD detector model No. LN/CCD-1024EHRB QE 75% at 900 nm, available from Princeton Instruments, of Trenton, N.J., USA. Camera 30 provides an output to a computer system 32.

The Raman spectra and associated autofluorescence background may be displayed on a display 33 of computer system 32 in real time and may be saved for further analysis. The prototype system acquires spectra over the wavenumber range of 800-1800 cm$^{-1}$ (a wavelength range of 838-914 nm).

Raman frequencies may be calibrated using materials having known Raman peaks in the spectral region of interest. For example the prototype system has been calibrated using the spectra of cyclohexane, acetone, and barium sulfate to an accuracy of 2 cm$^{-1}$. The spectral resolution of the prototype system is 8 cm$^{-1}$. All wavelength-calibrated spectra of the prototype system were also corrected for the wavelength-dependent response of the system using a standard lamp (model RS-10 available from EG&G Gamma Scientific, San Diego, Calif., USA).

Figure 2A:
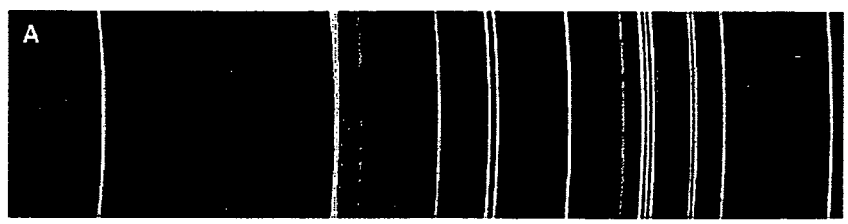
FIG. 2A shows curved spectral lines at the output of a spectrograph.

The image of a straight slit through a spectrograph that uses a planar grating has a curved parabolic line shape. This image aberration arises from the fact that rays from different positions along the length of the slit are incident on the grating at varying degrees of obliqueness. For spectrographs with short focal lengths, this obliqueness can cause significant distortion that can affect the measurement performance of the detector. For example, FIG. 2A shows the image aberration of a straight 100 µm slit through a spectrograph like the one used in the prototype system when illuminated by an Hg—Ar lamp. The curvature of the spectral lines is apparent in FIG. 2A. In the prototype system this curvature can be described by:

$$x = 1.1904E\text{-}5y^2 + 1.9455E\text{-}4y - 0.98613 \quad (1)$$

where x is the horizontal displacement of the line at a vertical position, y. The coefficients in Equation (1) are specific to the prototype system.

This image aberration presents two impediments to hardware binning of CCD columns: (1) it decreases the spectral resolution; and (2) it decreases the signal to noise ratio ("S/N") achievable. It also causes problems with wavelength calibration. "Hardware binning" is binning of intensities detected by CCD pixels performed before signal read-out by the preamplifier. For signal levels that are readout noise limited, such as for weak Raman signal measurements, hardware binning can improve S/N linearly with the number of pixels grouped together. Binning can also be done using software after the signal is read out. However, "software binning" improves the S/N only in proportion to the square root of the number of pixel values added together. Hence, complete hardware binning of an entire line is preferable to software binning for maximizing S/N. Combinations of hardware and software binning may also be used.

Figure 2B:
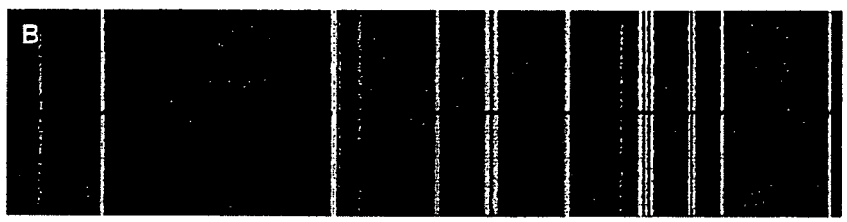
FIG. 2B shows lines at the output of a spectrograph which has been modified to correct for line curvature.

In the prototype, the image aberration discussed above was corrected by arranging 58 100-µm fibers of fiber bundle 24 along a curved line at the entrance of spectrograph 26. The curved line was formed by laser drilling holes in a stainless steel cylinder piece. The shape of the curved line corresponds to the horizontal displacement shown in Equation (1) but in the reverse direction. FIG. 2B shows a resulting CCD image of the output of spectrograph 26 with the fiber bundle illuminated by an Hg—Ar lamp. The central dark spots in each of the spectral lines of FIG. 2B correspond to the calibration fiber 27 that was not illuminated. The spectral lines are substantially straight, indicating effective image aberration correction. This permits each entire CCD vertical line (256 pixels in the prototype) to be hardware binned without losing resolution or reducing S/N.

Using the prototype system, an in vivo skin Raman spectrum can be obtained in less than 1 second. The illumination power density is 1.56 W/cm$^2$, which is less than the ANSI maximum permissible skin exposure limit of 1.63 W/cm$^2$ for 785 nm laser light.

Figure 3:
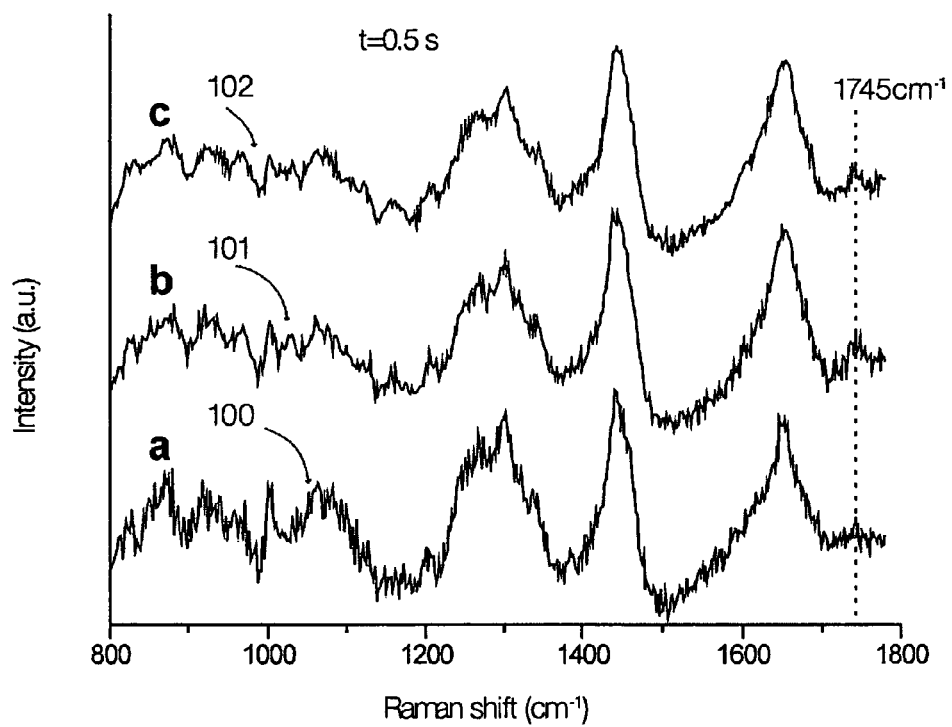
FIG. 3 shows Raman spectra of human skin for several binning modes.

Lines 100, 101 and 102 of FIG. 3 each show a Raman spectrum of the skin of a subject's palm. Line 100 is a spectrum resulting from the use of complete software binning. Line 101 is a spectrum acquired with combined hardware and software binning. Line 102 is a spectrum acquired using hardware binning. For all of lines 101, 101 and 102, a CCD integration time of 0.5 second was used. The S/N of the spectrum of line 102 can be observed to be significantly better than that of line 101 and is much better than that of line 100. The Raman peak at 1745 cm$^{-1}$ (from the C=O stretching band of lipid ester carbonyl) is barely visible in line 100, appears as a noisy small peak in line 101 and appears as a smooth well defined peak in line 102.

Overview of Method

Figure 4:
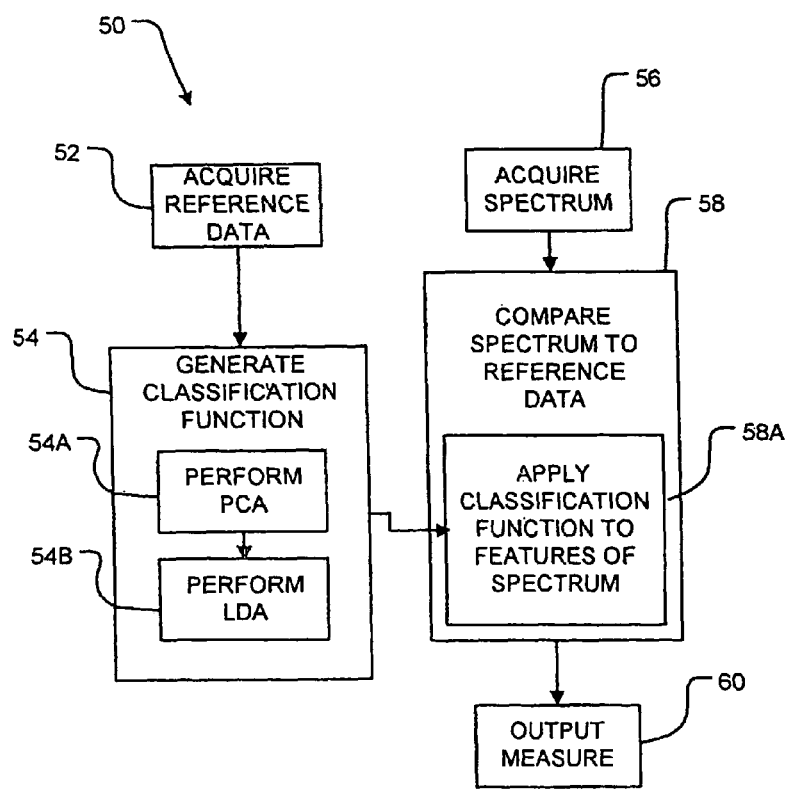
FIG. 4 is a flowchart illustrating a method of the invention.

FIG. 4 shows a method 50 according to an embodiment of the invention. Method 50 begins in block 52 by acquiring reference data. The reference data may be optical spectra of tissue samples. The reference samples may include tissues which are known to be normal and/or tissues which are know to be cancerous or otherwise abnormal. Suitable apparatus, for example, apparatus like that described above, is used to acquire the reference spectra. In block 54 a classification function is generated. The classification function takes as inputs features of a test spectrum and produces an output indicative of whether or not the tissue corresponding to the test spectrum is likely to be normal or abnormal. In the illustrated embodiment, block 54 includes performing Principal components analysis (PCA) (block 54A) and performing linear discriminant analysis (LDA) (block 54B).

Principal component analysis PCA and LDA are known data analysis techniques. PCA and LDA are described in various reference works including: Dillion R W, Goldstein M, *Multivariate analysis: methods and applications*, John Wiley and Sons, New York, 1984; and Devore J L, *Probability and statistics for engineering and the science*, Brooks/Cole, Pacific Grove. 1992.

In block 56, a test spectrum is acquired. The test spectrum may be acquired using suitable apparatus such as that described above. The test spectrum is of a section of tissue. The section of tissue may, for example, be an area of skin that has been identified as having an appearance that could possibly indicate cancer. In block 58 the test spectrum is compared to the reference data. In the illustrated embodiment, this comparison involves applying the classification function generated in block 54 to features of the test spectrum in block 58A. The features include both features of a Raman component of the test spectrum and features of a background fluorescence component of the test spectrum. The term background fluorescence is used herein to mean fluorescence in a wavelength range that includes peaks of a Raman spectrum.

In block 60 an output measure is provided. The output measure indicates a likelihood that the tissue section is normal or abnormal. The output measure may comprise any suitable indicator including one or more of:
- a graphical or textual value indicating a likelihood that the tissue section is normal or abnormal;
- a warning indicator, such as a warning light;
- graphical or textual information indicating a class into which the tissue section has been classified; or
- other suitable indicators.

Certain implementations of the invention comprise computer processors which execute software instructions which cause the processors to perform a method of the invention. For example, one or more processors in a computer system may implement the method of FIG. 4 by executing software instructions in a program memory accessible to the processors. The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like or transmission-type media such as digital or analog communication links. The instructions may optionally be in an encoded, encrypted and/or compressed format.

APPLICATION EXAMPLE #1

Figure 5:
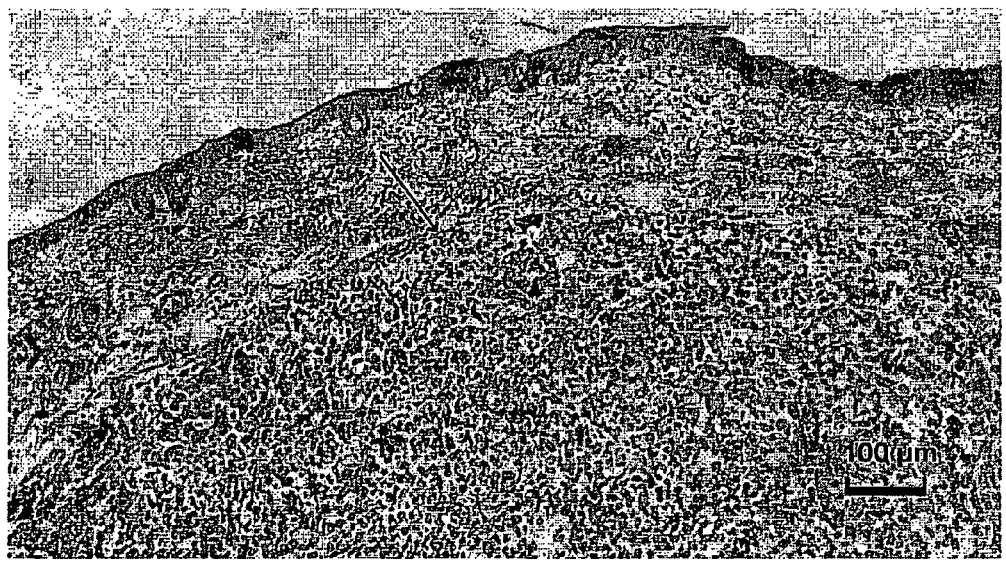
FIG. 5 is a microphotograph of a tumour in a mouse used as a test subject.

The diagnostic performance of NIR autofluorescence, Raman, and composite Raman and NIR autofluorescence (raw spectra) spectroscopy for in vivo tissue classification were studied using as a model a murine Meth-A fibrosarcoma model involving syngeneic BALB/c mice. Seven- to nine-week old female BALB/c mice each weighing 18-28 g were implanted subcutaneously with 1×10$^6$ Meth-A fibrosarcoma cells on the lower back. Tumors thus induced grew to approximately 5-6 mm in diameter at 7 days after inoculation, and were located approximately 200 μm beneath the skin surface (FIG. 5). For spectroscopic studies, the hair on the lower back of the mice was shaved, and the mice were immobilized in a holder designed to expose their back skin for spectroscopy measurements. Spectra were acquired in a pair-wise fashion from each mouse by measuring a tumor-bearing site and the normal-appearing skin approximately 5 cm away from the lateral border of the tumor.

Figure 6A:
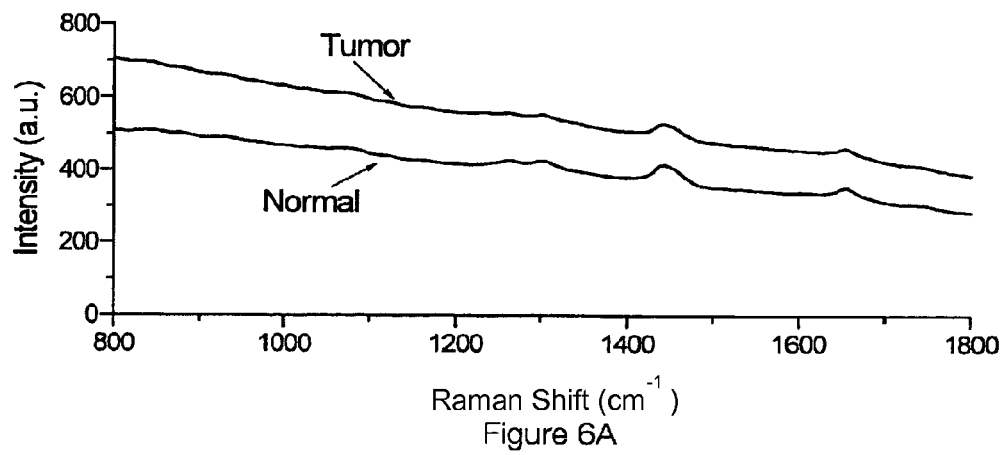
FIGS. 6A, 6B and 6C are respectively a raw spectrum from mouse tumour tissue; a background autofluorescence component of the raw spectrum of FIG. 6A and a Raman component of the raw spectrum of FIG. 6A.
Figure 6D:
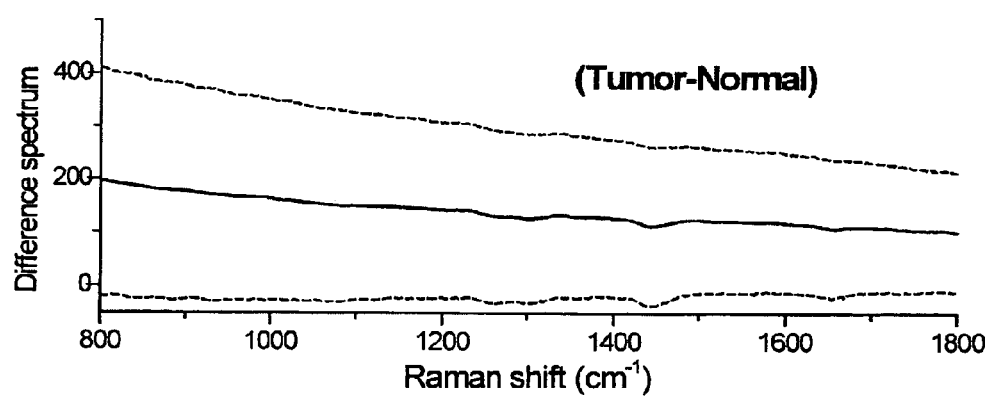
FIGS. 6D, 6E and 6F are respectively mean differences between tumor and normal tissues among individual mice corresponding to the raw spectrum and spectral components of FIGS. 6A, 6B and 6C respectively.
Figure 6B:
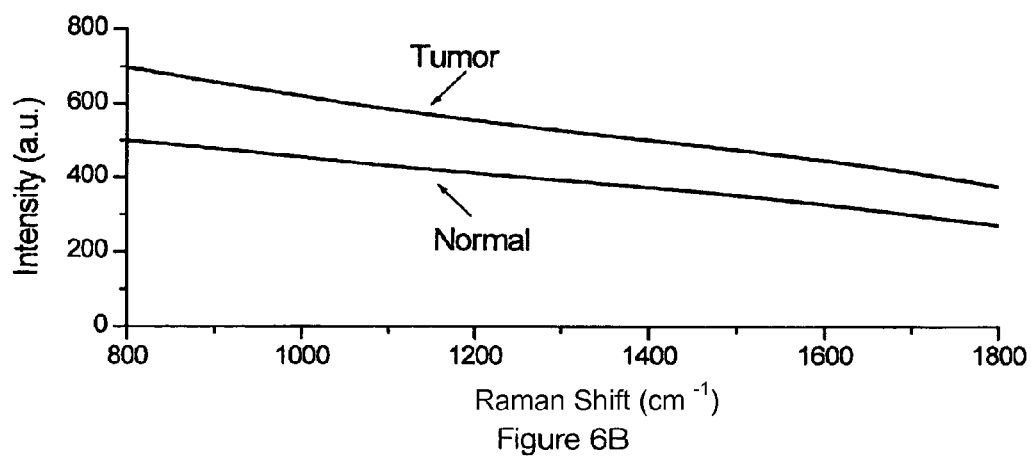
Figure 6E:
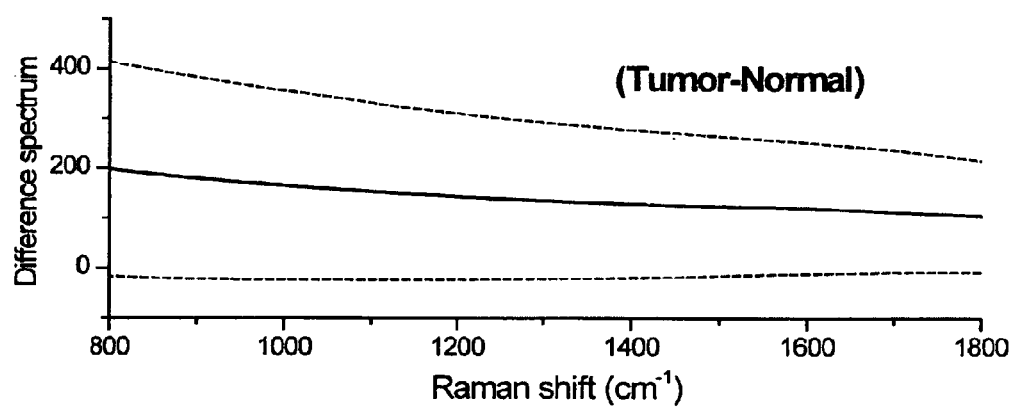
Figure 6C:
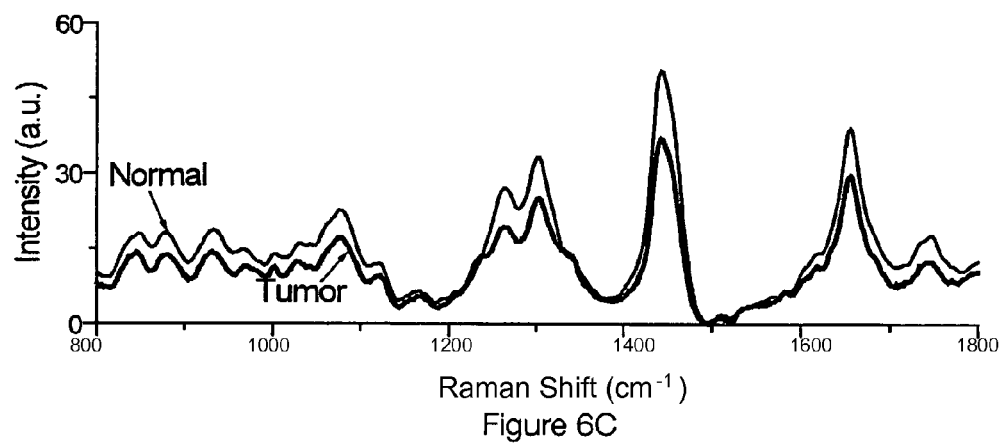

The raw spectra acquired from tissue in the 800-1800 cm$^{-1}$ Raman shift range included a prominent tissue autofluorescence component and a weaker tissue Raman scattering component, as shown in FIG. 6A. The raw spectra were preprocessed by adjacent 5-point smoothing to reduce noise. A fifth-order polynomial was fit to the broad autofluorescence background in the noise-smoothed spectrum (FIG. 6B). This polynomial, which essentially represents NIR autofluorescence was then subtracted from the raw spectrum to yield the tissue Raman spectrum alone (FIG. 6C). The following three data sets were thus produced:
- Raman (i.e., background-subtracted spectra),
- background autofluorescence alone (i.e., the 5$^{th}$ order polynomial), and,
- raw spectrum (composite Raman and NIR background autofluorescence spectra).

statistical analysis was performed using each of these data sets.

The entire spectral range (800-1800 cm$^{-1}$ Raman shift) was used for principal components analysis (PCA). Each spectrum was represented as a set of 497 intensities (PCA variables). To eliminate the influence of inter- and/or intra-subject spectral variability on PCA, the entire spectrum was standardized so that the mean of the spectrum was zero and the standard deviation of all the spectral intensities was one. This standardization ensures that the principal components (PCs) form an orthogonal basis.

The standardized data sets (i.e., Raman, autofluorescence, and raw spectra) were assembled into three separate data matrices with wavenumber (or wavelength) columns and a row for each individual animal. PCA was performed on the three standardized spectral data matrices to generate PCs comprising a reduced number of orthogonal variables that accounted for most of the total variance in the original spectra. Each PC is related to the original spectrum by a variable called the PC score, which represents the weight of that particular component against the basis spectrum.

Paired two-sided student t-tests as described, for example, in Devore J L, *Probability and statistics for engineering and the sciences*, Brooks/Cole, Pacific Grove, 1992. were used to identify diagnostically significant PC scores for each case using an alpha of 5%. All statistically significant PC scores were retained and then input into a LDA model for tissue classification.

LDA determines the discriminant function line that maximizes the variance in the data between groups while minimizing the variance between members of the same group. The performance of the classification functions resulting by the LDA models was estimated in an unbiased manner using the leave-one-out, cross-validation method as described, for example, in Dillion R W and Goldstein M, *Multivariate analysis: methods and applications*, John Wiley and Sons, New York, 1984 and Lachenbruch P and Mickey R M, *Estimation of error rates in discriminant analysis*, Technometrics 1968; 10:1-11. In this method, one spectrum was removed from the data set and the entire algorithm including PCA and LDA was performed using the remaining tissue spectra to produce a new classification function. The new classification function was then used to classify the withheld spectrum. This process was repeated until all withheld spectra were classified. The results of this analysis indicated the relative ability to correctly predict the status (i.e., tumor vs. normal) based upon each of the model spectra.

To compare the performance of the PCA-LDA model for tissue classification using the three spectroscopic data sets (Raman, autofluorescence, and raw spectra), receiver operating characteristic (ROC) curves were generated by successively changing the thresholds to determine correct and incorrect classifications for all subjects.

All multivariate statistical analyses were performed using Factor Analysis and Stepwise Discriminant Analysis modules within the BMDP statistical software package (Version 7.0, BMDP Statistical Software, Inc., Los Angeles, Calif.).

Figure 6F:
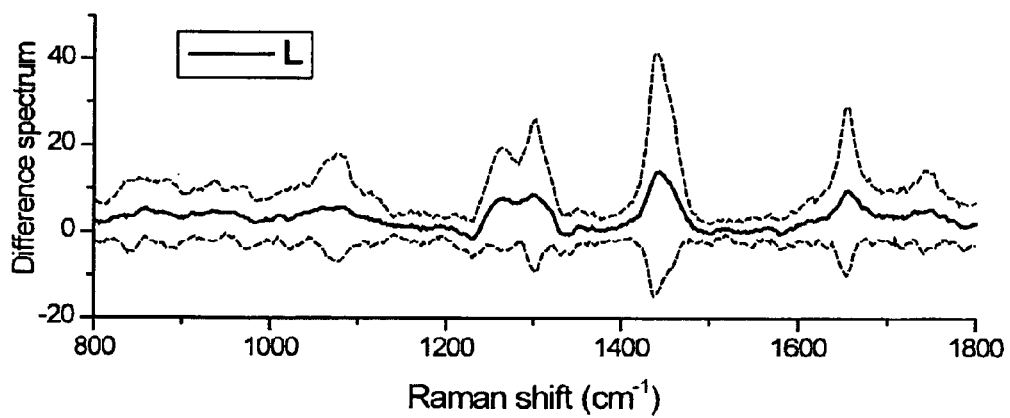

On average, the raw spectra and the background autofluorescence spectra showed higher signal intensities for tumor than for normal skin, whereas the converse was true for Raman scattering (see FIGS. 6A, 6B, and 6C). Compared to normal surrounding tissue, tumor tissue was significantly associated with an increased overall intensity of autofluorescence background spectra (p<0.0001; paired student t-test on the mean differences of spectral intensities point by point in the range 800-1800 $cm^{-1}$ between normal and tumor tissue) (FIGS. 6A, 6B), whereas normal skin exhibited higher Raman intensity than tumor tissue (P<0.0001; paired student t-test) (FIG. 6C). Nevertheless, there was significant variability for the spectrum differences across separate animals as reflected in the mean difference spectra SD (FIGS. 6D, 6E and 6F. These differences made it impractical to differentiate between normal and tumor tissue using overall signal intensities alone.

It can be seen that the raw spectrum of FIG. 6A is composed of a small contribution of tissue Raman scattering superimposed on a relatively intense autofluorescence background. The mean in vivo Raman spectra for tumor and normal skin (FIG. 6C) showed similar vibrational bands that were dominated by several prominent Raman peaks. For instance, the Raman bands observed in both tumor and normal skin at Raman shifts of 1655 $cm^{-1}$, 1445 $cm^{-1}$, 1300 $cm^{-1}$, 1265 $cm^{-1}$, and 1004 $cm^{-1}$ are presumably attributed to the protein amide I, $CH_2$ bending modes, $CH_2$ twisting modes, protein amide III, and phenyl ring breathing mode, respectively. Tentative assignments of some Raman bands observed in tumor and normal skin are summarized in Table 1.

TABLE I

ASSIGNMENT OF RAMAN BANDS

| Peak position ($cm^{-1}$) | Protein assignments | Lipid assignments | Others |
|---|---|---|---|
| 1745w | | $\nu(C=O)$ | |
| 1655vs | $\nu(C=O)$ amide I (a-helix conformation, collagen) | | |
| 1620w | | | $\nu(C=C)$ porphyrin |
| 1585vw | $\nu(C=C)$ olefinic | | |
| 1558vw | $\nu(CN)$ and $\delta(NH)$ amide II | | $\nu(C=C)$ porphyrin |
| 1514 | | | $\nu(C=C)$ carotenoid |
| 1445vs | $\delta(CH_2)$, $\delta(CH_3)$ | $\delta(CH_2)$ scissoring | |
| 1379vw | | $\delta(CH_3)$ symmetric | |
| 1336mw (sh) | $\delta(CH_2)$, $\delta(CH_3)$, twisting, collagen | | |
| 1302vs | $\delta(CH_2)$ twisting, wagging, collagen | $\delta(CH_2)$ twisting, wagging | |
| 1265s | $\nu(CN)$ and $\delta(NH)$ amide III (a-helix conformation, collagen) | | |
| 1208vw | $\nu(C-C_6H_5)$ phenylalanine | | |
| 1168vw | | $\nu(C=C)$, $\delta(COH)$ | $\nu(C-C)$, carotenoid |
| 1122mw (sh) | | $\nu_s(CC)$ skeletal | |
| 1078ms | | $\nu(CC)$ skeletal | $\nu(CC)$, $\nu_s(PO_2^-)$ nucleic acids |
| 1030mw (sh) | $\nu(CC)$ skeletal, keratin | | |
| 1004mw | $\nu(CC)$ phenylalanine ring | | |
| 973mw (sh) | $r(CH_3)$, $\delta(CCH)$ olefinic | | |
| 935mw | $r(CH_3)$ terminal, proline, valine; $\nu(CC)$ a-helix keratin | | |

TABLE I-continued

ASSIGNMENT OF RAMAN BANDS

| Peak position (cm$^{-1}$) | Protein assignments | Lipid assignments | Others |
|---|---|---|---|
| 883mw | r(CH$_2$) | | |
| 855mw | δ(CCH) phenylalanine, olefinic | | polysaccharide | v, stretching mode; vs, symmetric stretch; vas, asymmetric stretch; δ, bending mode; r, rocking mode; v, very; s, strong; m, medium; w, weak; sh, shoulder The shape of the background autofluorescence spectrum in the range of 800-1800 cm$^{-1}$ (i.e., 838-914 nm) can be seen to differ between tumor and normal skin (FIG. 6B). The ratio of the curves for normal and tumor tissue is not a flat horizontal line but decreases from 800 cm$^{-1}$ to 1350 cm$^{-1}$ and then increases until close to 1800 cm$^{-1}$ (data not shown). Although no distinctive differences in Raman peak positions were observed between normal and tumor tissue, subtle differences in spectral lineshapes were noted, especially at 1200-1400 cm$^{-1}$ and 1500-1650 cm$^{-1}$. PCA/LDA is one way to exploit such lineshape differences for tissue classification.

Figure 7A:
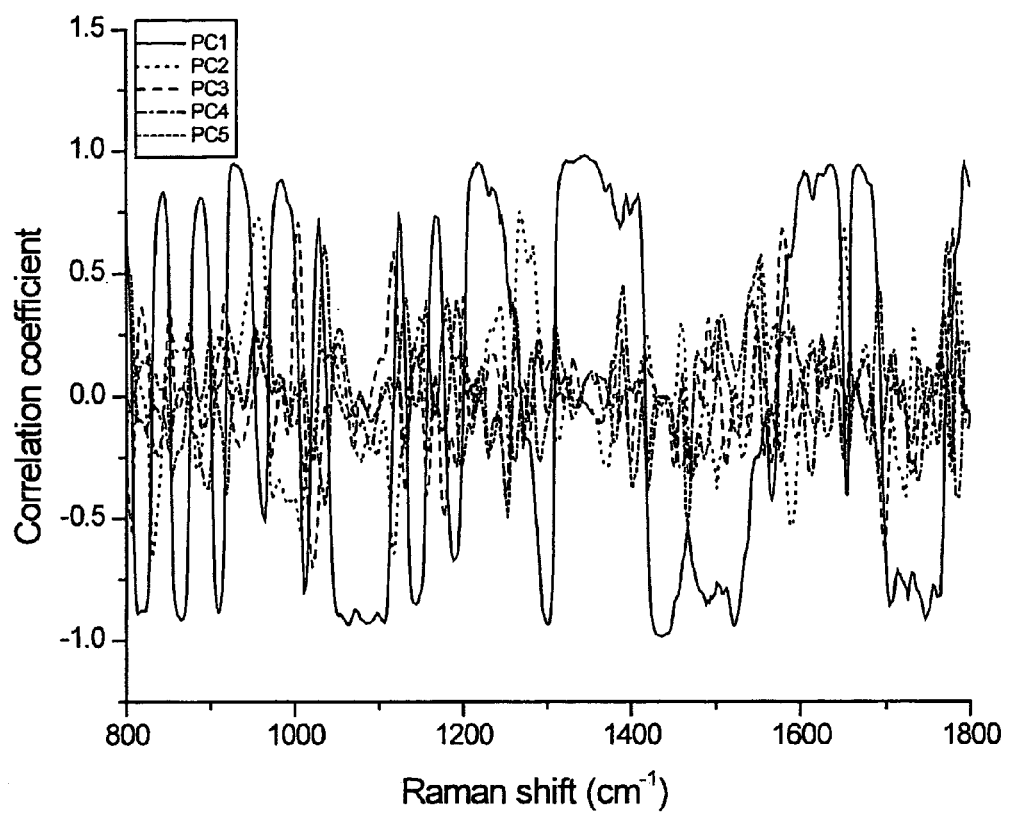
FIGS. 7A, 7B and 7C are respectively plots of principle components for Raman, background fluorescence, and raw spectra.
Figure 7B:
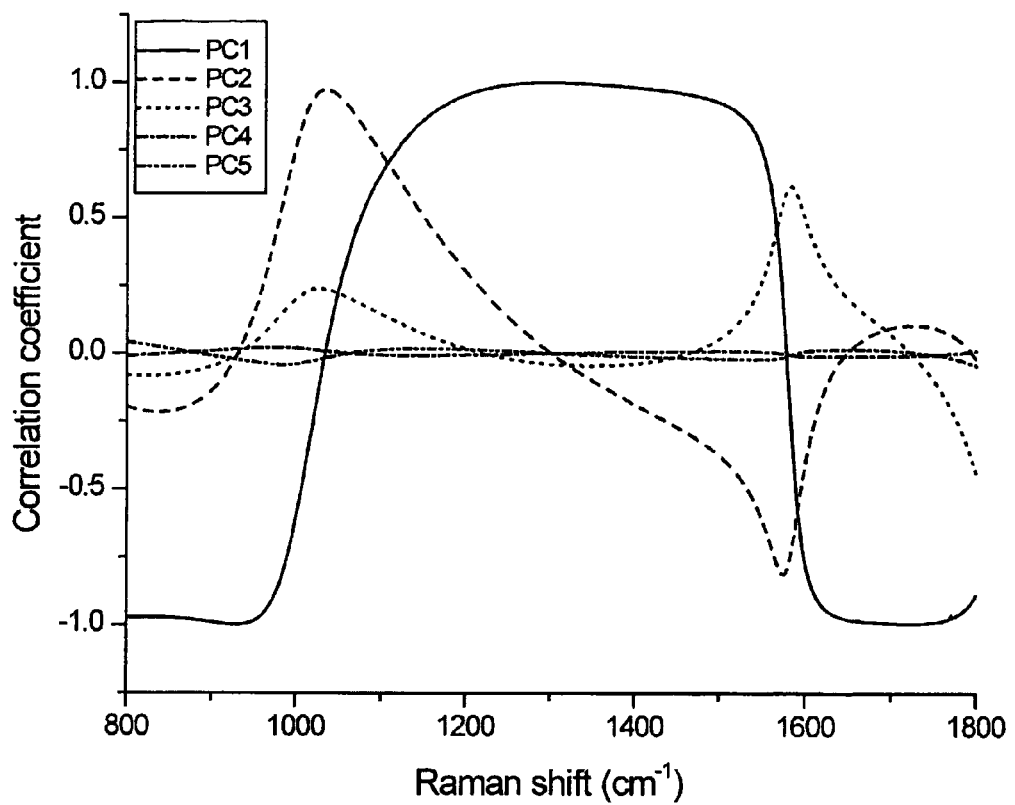
Figure 7C:
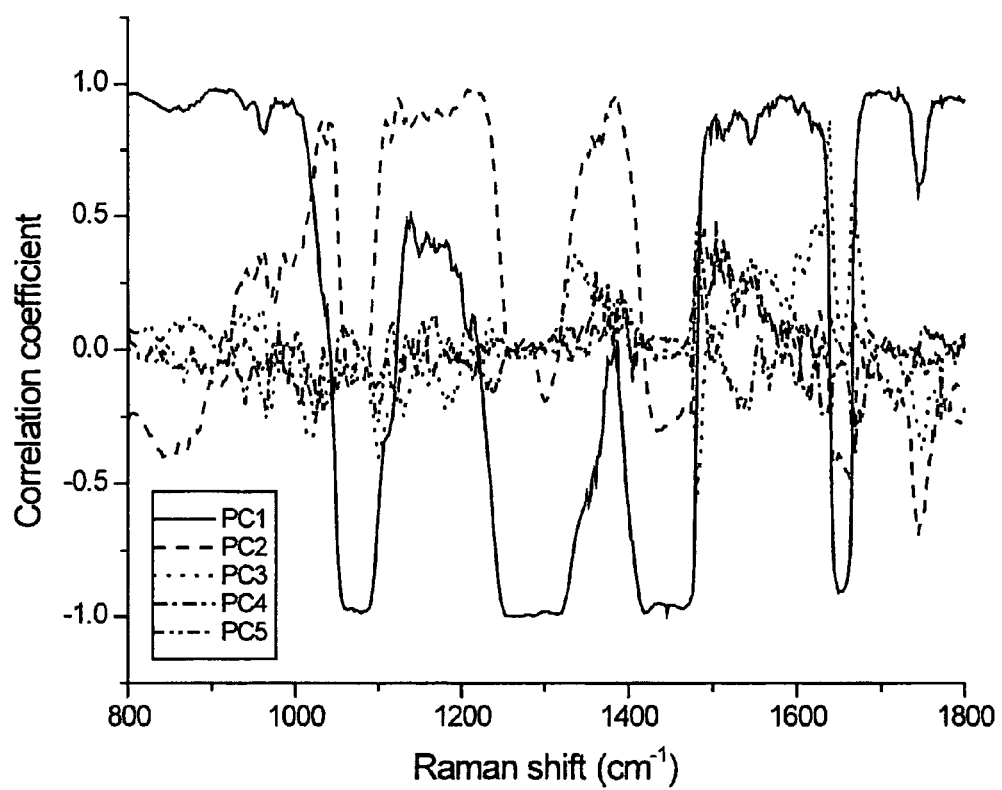

FIGS. 7A through 7C show respectively the first five principal components (PCs) loadings calculated from principal component analysis (PCA) for:
Raman spectra;
background autofluorescence spectra; and,
raw spectra.

Overall, the PC features for each of the three spectral data sets differ from those of the other spectral data sets. Some PC features (FIGS. 7A, 7C) roughly correspond to Raman spectra, with peaks at positions similar to those at which Raman peaks occur in skin tissue. The first PC accounts for the largest variance within the spectral data sets (e.g., 74.6% for Raman; 79.5% for autofluorescence; 69.9% for raw spectra), whereas successive PCs describe features that contribute progressively smaller variances.

Figure 8A:
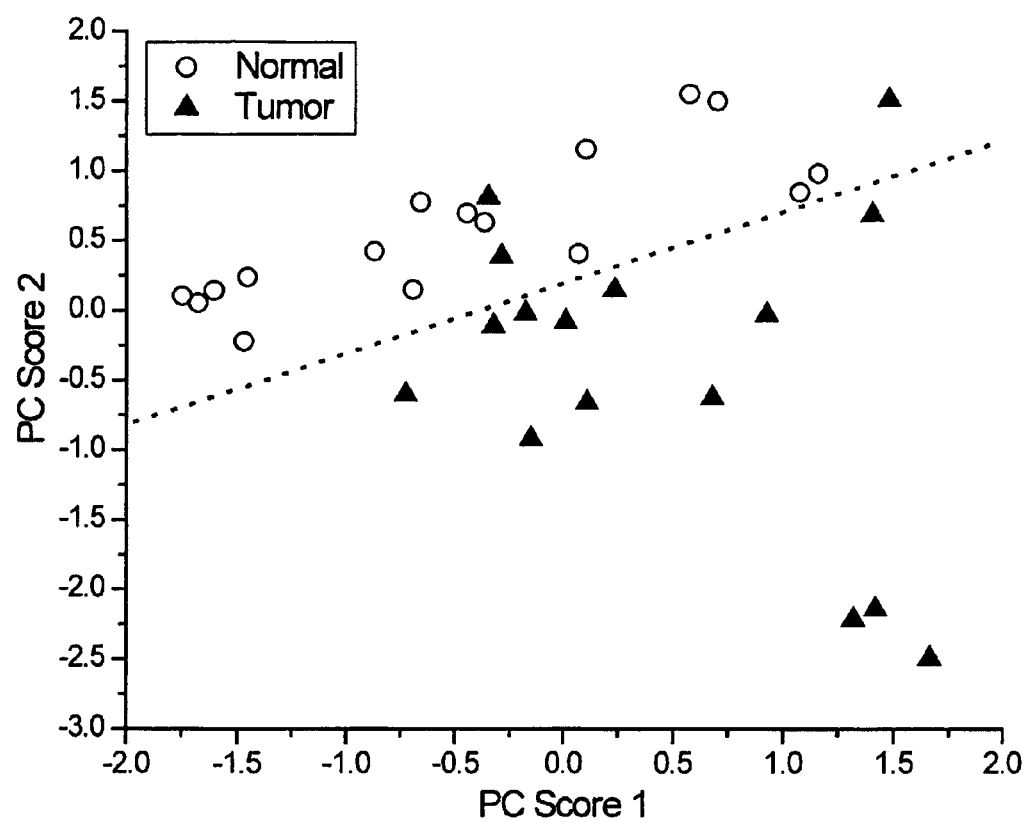
FIGS. 8A, 8B and 8C are scatter plots of the two most diagnostically significant principal components for Raman, background fluorescence and raw spectra respectively.
Figure 8B:
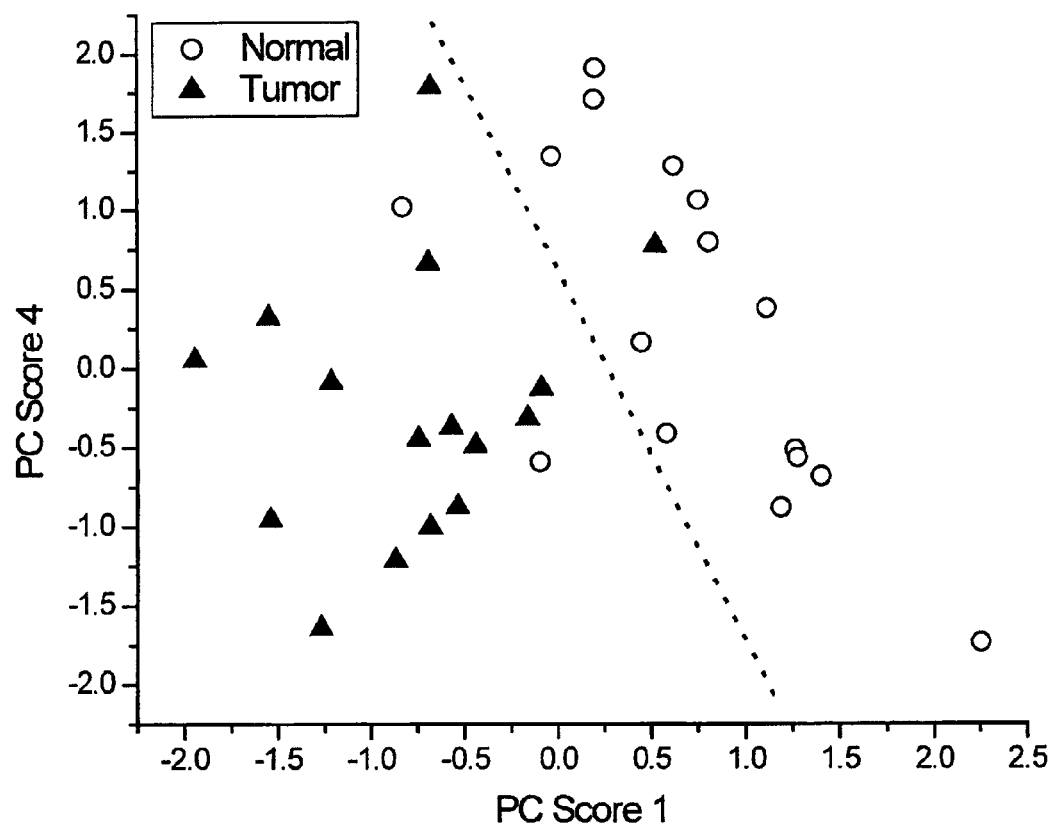
Figure 8C:
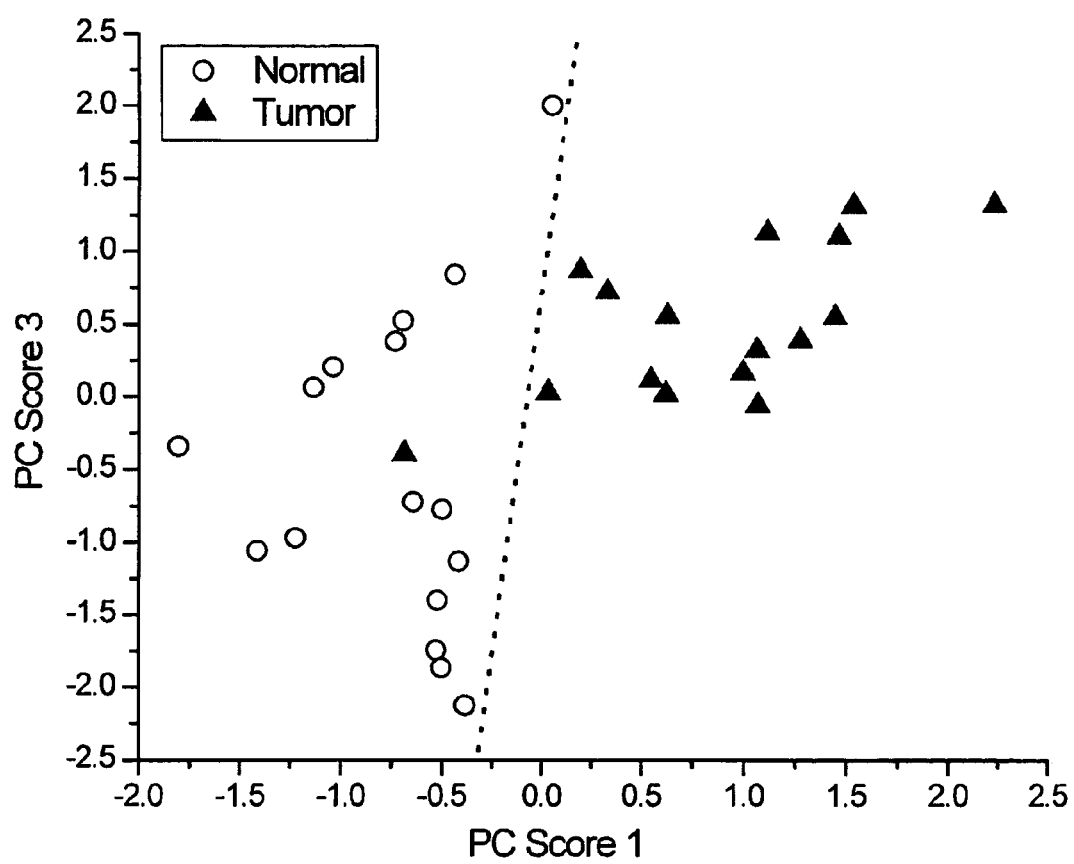
Figure 9A:
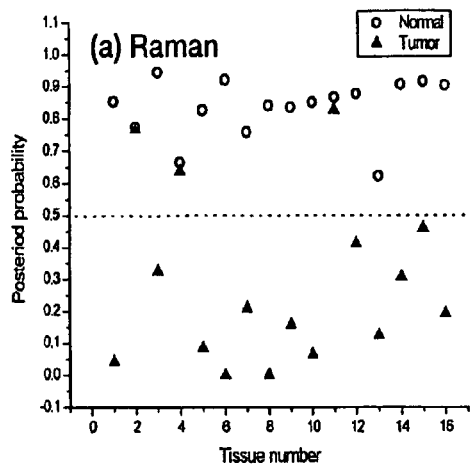
FIGS. 9A, 9B, 9C and 9D are plots of posterior probabilities of belonging to normal and tumor groups calculated respectively for Raman, background autofluorescence, raw spectra, and combined Raman PC scores and NIR background fluorescence PC scores.
Figure 9B:
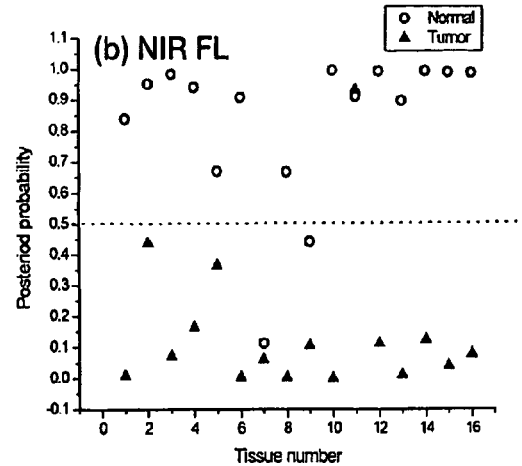
Figure 9C:
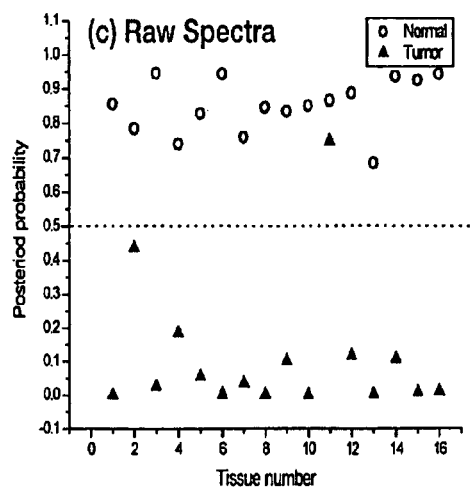
Figure 9D:
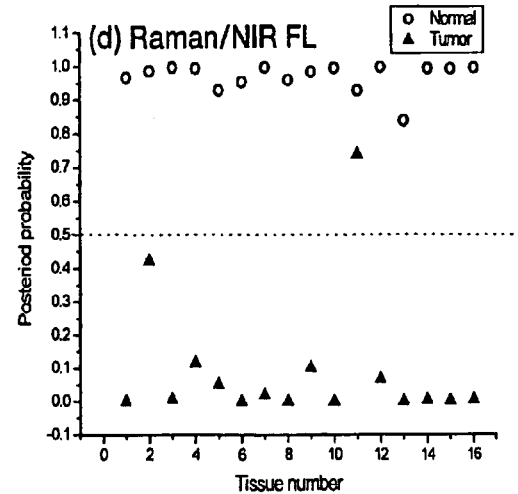

Paired two-sided student t-tests on the first five PC scores comparing normal and tumor-bearing skin showed that there were only three PCs (PC1, PC2, PC3 in FIG. 7A), two PCs (PC1, PC4 in FIG. 7B), and three PCs (PC1, PC3, PC4 in FIG. 7C) that were diagnostically significant (p<0.0001) for discriminating normal and malignant tissues. FIGS. 8A, 8B, and 8C show examples of scatter plots of the most diagnostically significant PC scores for normal and tumor tissue derived respectively from:
Raman (PC1 vs. PC2);
background autofluorescence (PC1 vs. PC4); and,
raw spectra (PC1 vs. PC3).

These Figures show that the spectra can be clustered into normal and tumor groups using dotted lines that represent potential diagnostic algorithms. In this case the dotted lines represent a set of linear combinations of two PC scores that could be used as a classification function.

LDA was used to generate classification functions using all significant PCs for each of the 3 different spectral data sets. Based on the statistically significant spectral features in each data set, classification functions using PCA-LDA-based spectral classification with leave-one-out, cross-validation method were developed. Posterior probabilities were determined by calculating the percentage of each group in the data set by LDA. The cost of misclassifying normal skin as tumor was chosen to be 0.50 for the maximal number of correctly classified tissue groups.

FIGS. 9A, 9B, 9C and 9D show the posterior probabilities of belonging to the normal and tumor groups as calculated respectively for:
Raman;
background autofluorescence;
raw spectra; and,
a combination of the Raman spectrum PC scores and background autofluorescence spectrum PC scores.

The classification results showed that 81.3% (13/16), 93.8% (15/16), 93.8% (15/16) and 93.8% (15/16) of tumor tissue are correctly classified (diagnostic sensitivity) with a posterior probability less than 0.50 using the four types of data (i.e., Raman; NIR autofluorescence; raw spectra; and Raman spectra PC scores and NIR autofluorescence spectra PC scores combined), respectively. The diagnostic specificities are 100%, 87.5%, 100%, and 100%. Overall diagnostic accuracies are 90.6%, 90.6% and 96.9% and 96.9% for the Raman spectra, NIR background autofluorescence spectra, raw spectra and Raman spectra PC scores and NIR Autofluorescence spectra PC scores combined respectively. It is noteworthy that the raw spectra, which includes both Raman and background fluorescence components, has a better overall diagnostic accuracy than either the Raman spectra or background autofluorescence spectra taken alone.

Figure 10:
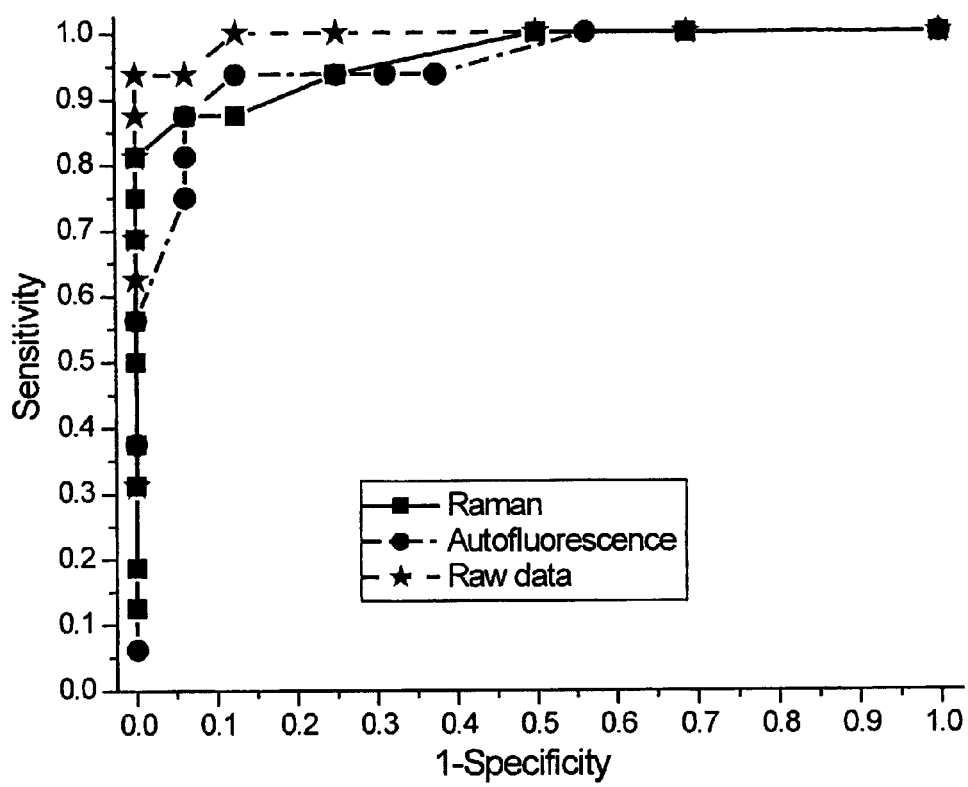
FIG. 10 is a set of receiver operating characteristic curves generated for Raman, background autofluorescence, raw spectra, and combined Raman PC scores and NIR background fluorescence PC scores at different threshold levels.

To further evaluate and compare the performance of the PCA/LDA-based classification functions derived from the four types of data for in vivo tissue classification, receiver operating characteristic (ROC) curves (FIG. 10) were generated from the scatter plots in FIGS. 9A to 9D at different threshold levels. FIG. 10 shows the discrimination results using Raman, NIR autofluorescence, raw spectra, and a Raman spectra PC scores and NIR Background autofluorescence PC scores combined. A comparative evaluation of the ROC curves indicates that either NIR autofluorescence or Raman alone can be used for in vivo tissue diagnosis with high diagnostic sensitivity and specificity. However, of the classification functions derived from the four types of data, it appears that the classification function derived from the raw spectra (which which is a composite of Raman and NIR fluorescence spectra components) or the classification function derived from combined Raman spectra PC scores and NIR background autofluorescence PC scores can give the most effective diagnostic capability for in vivo tissue classification, this is illustrated by the improvement in the specificity and sensitivity. The integration areas under the ROC curves are 0.951, 0.963, 0.994 and 1.0. for classification functions derived respectively from: NIR background autofluorescence; Raman spectra; raw spectra; and Raman spectra PC scores and NIR background autofluorescence PC scores combined. The results suggest that the raw spectra, which contains both Raman signatures and NIR autofluorescence signatures may generate better diagnostic accuracy than either the Raman or NIR background autofluorescence modalities taken alone.

Multivariate statistical analysis allows objective diagnosis by retaining only those principal components that describes inter-group differences. The information most useful for tissue diagnosis is distributed only over a few PCs. For LDA models, the discriminative information may be contained in the first 3-4 PCs. PCA plots of significant PC scores (See FIGS. 8A to 8C) show that the combination of tissue NIR autofluorescence and Raman spectra correlate well with pathologic grouping.

PCs that describe most of the variance in the spectroscopic data do not necessarily provide the most diagnostic utility. For instance, for the background autofluorescence data set, one of the most significant PCs (PC4) describes only 0.33% of the total variance. While the inventors do not wish to be bound by any specific theory of operation, this suggests that subtle modifications in histochemistry precede and accompany significant pathological changes to the tissue. Other PCs that explain only very small amounts of the total variance but are diagnostically significant were also found in the Raman and raw spectral data sets.

The combination of PCA and LDA is a statistically powerful tool for providing diagnostic tissue classification algorithms having high diagnostic sensitivity and specificity based on features of background autofluorescence and Raman spectra.

While the inventors do not wish to be bound by any particular theory of operation, the favorable discriminant results obtained by employing the raw spectra, which contain both autofluorescence and Raman signatures might be explained as follows: NIR autofluorescence has previously been treated as useless background signals in the measured raw spectra but, as the inventors have learned, the NIR autofluorescence enhances the ability to differentiate tumor from normal tissue, and may be useful for establishing the chemical identity of the NIR fluorophores in tissue. The combination of Raman spectra, which respond to vibrational modes in materials within tissues, with the autofluorescence signals using PCA/LDA can be a powerful tool for elucidating the biochemical structure and composition of tissue, and thus may provide useful diagnostic capabilities for tissue diagnosis.

The use of NIR Raman and NIR Background fluorescence spectra as a diagnostic tool has advantages over diagnostic tools which require a subject to be irradiated with UV light. Unlike UV excitation light, NIR light is non-carcinogenic, and it is safe for use in tissue diagnosis. Further, where both the incident light used and the measured tissue autofluorescence and Raman light are at NIR wavelengths, the light can penetrate deeper into the tissue (e.g. up to about 1 mm) than light at other wavelengths. Therefore, NIR autofluorescence and Raman spectroscopy are potentially useful for the non-invasive in vivo detection of lesions located below the surface of tissue. For example, lesions could be detected by NIR autofluorescence imaging, and then characterized by Raman spectroscopy.

APPLICATION EXAMPLE #2

Figure 11:
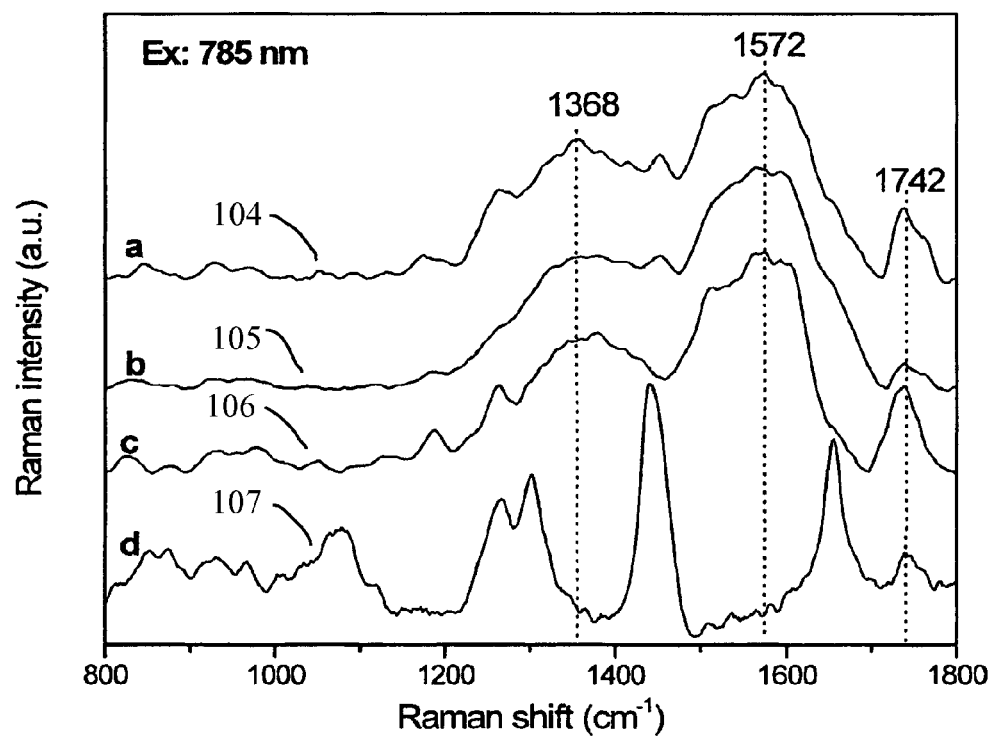
FIG. 11 shows Raman spectra of various skin areas, both cancerous and not cancerous.

As shown in FIG. 11, some features of Raman spectra are different between normal to benign (compound nevus) and malignant (melanoma) skin diseases. Curve 104 is a Raman spectrum of the volar forearm normal skin of a subject of African descent. Curve 105 is a Raman spectrum of a benign compound pigmented nevus. Curve 106 is a Raman spectrum of a malignant melanoma. Curve 107 is a Raman spectrum of normal skin adjacent the melanoma of curve 106. One can see significant differences between these curves. The 1445 $cm^{-1}$ peak is not visible in the malignant melanoma spectrum 106 but can be seen in both the normal black skin spectrum 104 and the benign compound nevus spectrum 105. The 1269 $cm^{-1}$ peak is present in the malignant melanoma spectrum 106 and in the normal black skin spectrum 104 but not in the benign compound nevus spectrum 105. Features of these curves may be used together with features of NIR autofluorescence which forms a background to these curves in the raw spectra from which these curves are extracted in a classification method according to this invention.

APPLICATION EXAMPLE #3

Some methods of the invention provide a plurality of classification functions. Such methods may involve selecting the one of the classification functions most appropriate for classifying the tissue section involved. For example, the classification functions may include classification functions for any one or more of:

- a number of different pathologies (such as, for example, two or more of basal cell carcinoma (BCC), squamous cell carcinoma (SCC), melanoma, actinic keratosis, seborrheic keratosis, sebaceous hyperplasia, keratoacanthoma, lentigo, melanocytic nevi, dysplastic nevi, and blue nevi);
- a number of different tissue types (such as, for example, two or more of skin, lung tissue, other epithelial tissues, such as the bronchial tree, the ears nose and throat, the gastrointestinal tract, the cervix, and the like);
- a number of different skin types (for example, one classification function may be provided for use with subjects having lightly pigmented skin and another classification function may be provided for use with subjects having more darkly pigmented skin; and,
- a number of different locations on the body of the same general tissue type (for example, as described below, different classification functions may be provided for classifying skin for different areas of a subject's body.

Where a plurality of classification functions are provided, each of the classification functions may be derived from a set of reference data for the tissue type/medical condition/tissue location for which the classification function is intended to be used. Apparatus according to the invention may include a user interface which permits a user to select an appropriate one of a plurality of classification functions.

Figure 12:
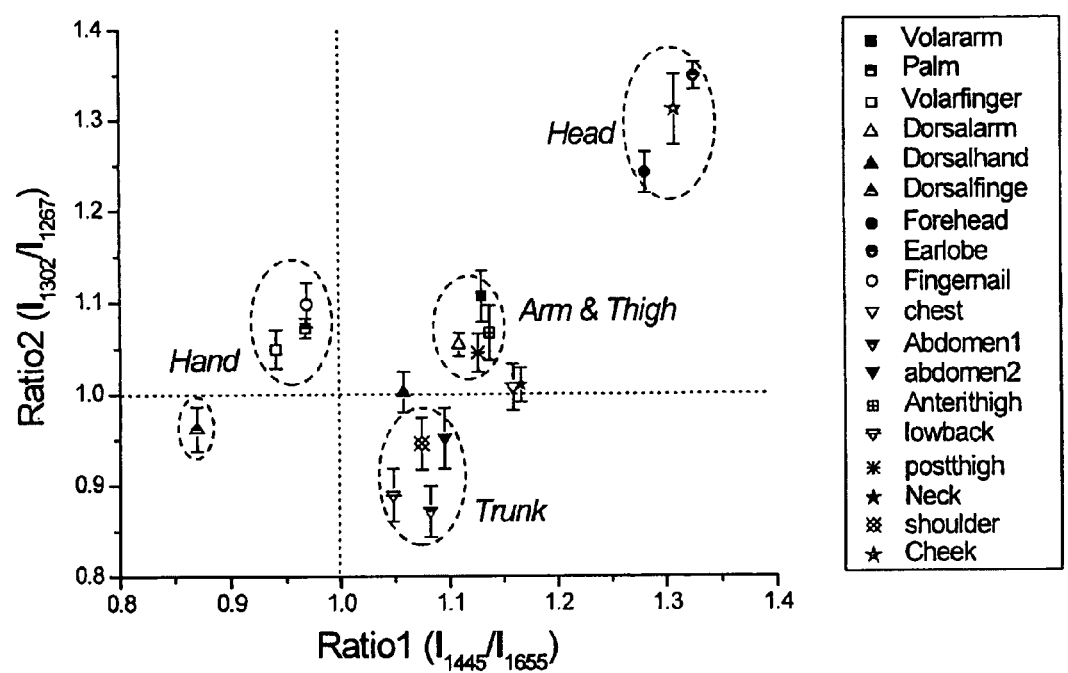
FIG. 12 is a scatter plot relating two ratios of lipid-to-protein Raman bands showing clustering behaviour for Raman spectra acquired at different locations on subjects' bodies.
Figure 13:
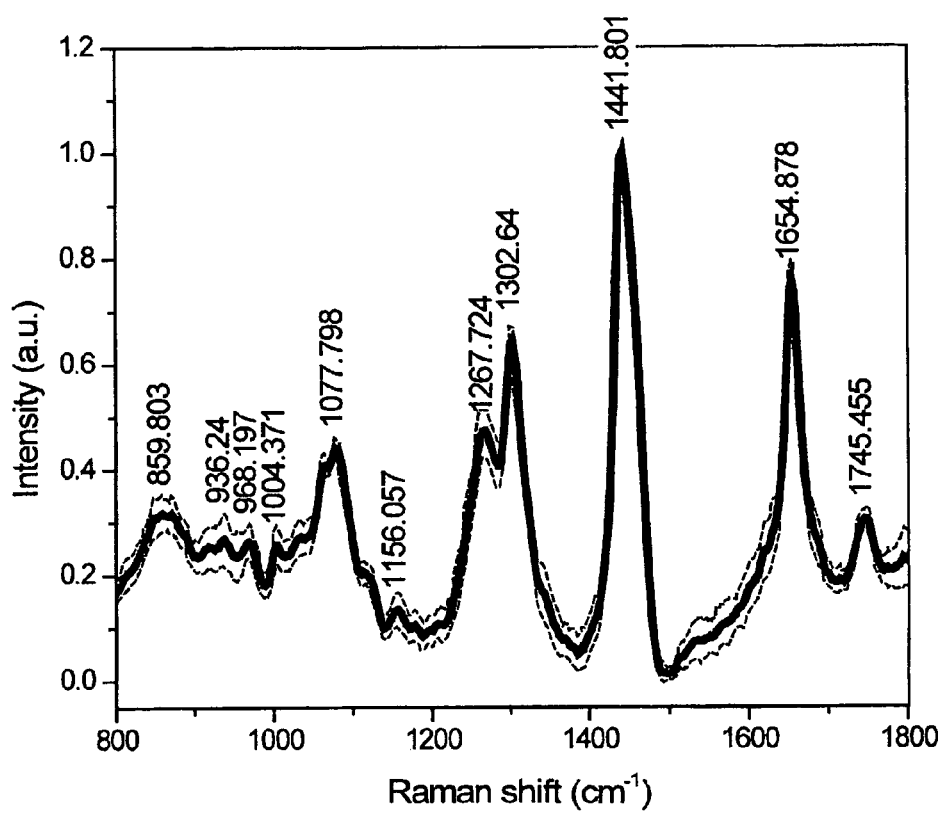
FIG. 13 shows variation among Raman spectra of skin taken at the same body location in a number of different subjects.

The inventors have learned that, within the same subject, the Raman spectrum of skin is typically significantly different for different body sites. In some embodiments of the invention a classification function is selected based on a body site in which a tissue being studied is located. Raman spectroscopy measurements were taken at each of 25 body sites for each on 50 normal volunteers. FIG. 12 shows ratios of lipid-to-protein Raman bands for the Raman spectroscopy measurements. It can be seen that these ratios are clustered according to body sites. As shown in FIG. 13, the inter-subject differences of skin Raman signals for a given body site are relatively small, at least for subjects having lightly pigmented skin.

This observation may be applied in the practice of this invention by providing a plurality of different classification functions each corresponding to a different body location. The different classification functions may each be developed using reference Raman and background fluorescence spectra obtained at the corresponding body locations. The appropriate classification function may be selected based upon the body location from which a test spectrum is obtained. By way of example, different classification functions may be provided for a plurality of different body regions which may include, for example, the hands; the head; the arms and torso; and the thighs. Classification functions developed from reference data from other skin regions, such as the feet, legs and nails may also be provided.

APPLICATION EXAMPLE #4

A patient has a condition such as dysplastic nevus. The condition causes many nevi at various locations on the patient's body. The patient visits his physician who needs to decide whether it is necessary to take a biopsy of any of the nevi and, if so, which ones. There are enough nevi that it is not desirable or practical to take biopsies of all of the nevi.

The physician obtains a NIR spectrum for each of the nevi to be investigated. The NIR spectra include both Raman features and NIR fluorescence features. The spectra may be obtained, for example, with apparatus as described above and shown in FIG. 1. The physician can place the probe of the apparatus on each nevus in turn and then trigger the acquisition of a spectrum by activating a control. For example, the physician may press a button when the probe is over a nevus and then hold the probe over the nevus until a spectrum has been acquired. The apparatus may generate a signal, such as an audible beep, when the spectrum has been acquired. If the apparatus is configured to take into account differences between one or more Raman and/or NIR background autofluorescence features of a spectrum of the nevus being investigated and corresponding features of normal tissue of the patient then the physician also obtains a spectrum from a portion of the patient's skin which appears to be normal.

The apparatus either includes or is connected to a computer system capable of applying classification functions to the spectra acquired from various sites on the patient. Prior to applying the classification function to the acquired spectrum, the physician may use an interface provided by the computer system to select a classification function appropriate for classifying dysplastic nevi on the patient. The interface may prompt the physician to answer questions to follow a decision tree resulting in selection of the appropriate classification function. In the alternative, the interface may permit the physician to directly select a classification function or to input data on the basis of which the computer system can select the most appropriate classification function.

The computer system applies the classification function to each of the acquired spectra. This may be done immediately after acquiring one spectrum and before acquiring the next spectrum or in a batch mode after a number of spectra have been acquired. For each spectrum, the computer system provides an output signal indicative of whether the classification function indicates that the corresponding nevus is likely to be normal or is likely to be abnormal. The output may comprise a visible or audible signal. The output may be a simple output which simply indicates whether the spectrum is indicative of normal tissue or suggests that the tissue may be abnormal. In the alternative, the output may comprise numeric and/or graphical information which indicates a likelihood that the tissue from which the spectrum was taken is normal or abnormal.

The physician can use the output to decide which of the patient's nevi, if any, should be more thoroughly studied by way of a biopsy or other procedure.

APPLICATION EXAMPLE #5

A patient suspected of having lung cancer undergoes bronchoscopy. A bronchoscope is equipped with an endoscopic probe capable of acquiring a spectrum having Raman and background fluorescence features. Suitable probes are described, for example, in Zeng, U.S. Ser. No. 10/761,703 and PCT CA/04/00062. The physician positions the tip of the bronchoscope adjacent a tissue section of interest and triggers the apparatus to obtain a spectrum. The apparatus applies a classification function to the spectrum. The classification function is appropriate for lung tissue. The classification function may have been developed from a set of reference spectra including normal lung tissue and lung tissue known to be cancerous. The apparatus provides an output. The physician can use the output together with images acquired by the bronchoscope to select locations for taking biopsy samples.

APPLICATION EXAMPLE #6

Figure 18:
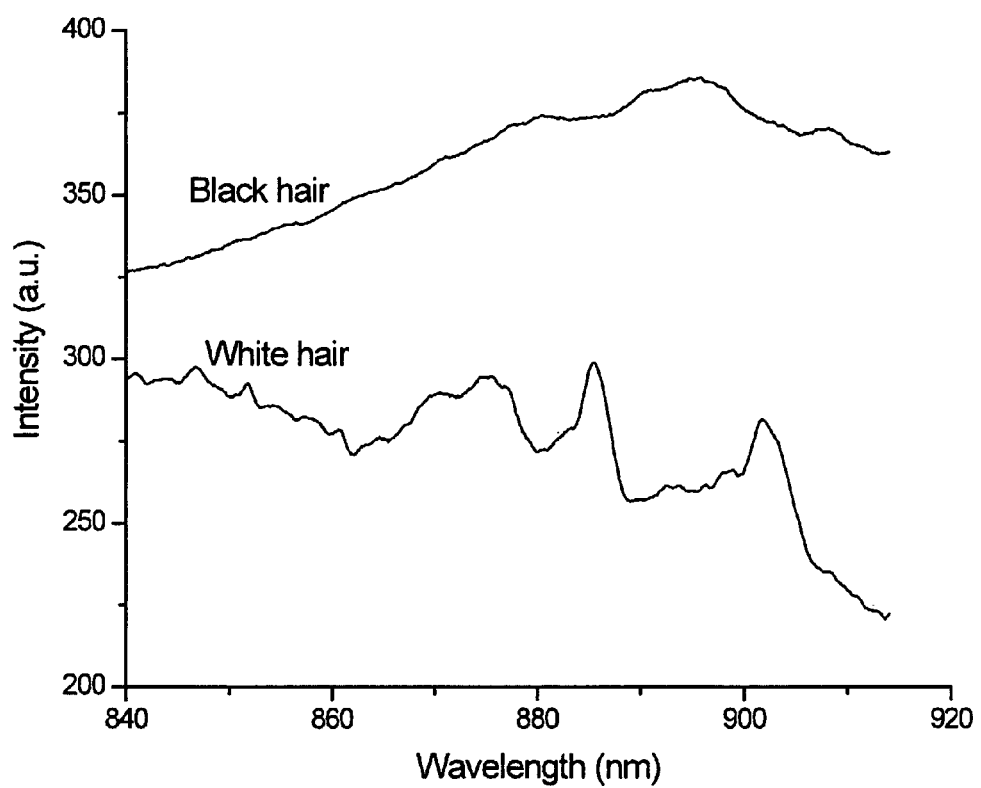
FIG. 18 compares NIR spectra for black and white hairs.

In some cases, it is useful to measure the melanin content of a tissue. The inventors have determined that melanin has broad Raman peaks at Raman shifts of approximately 1380-1400 $cm^{-1}$ and 1580-90 $cm^{-1}$. These peaks can be detected in the Raman spectra of human hair, which contains melanin (see FIG. 18). These peaks may be used to measure melanin content of tissues.

Figure 14:
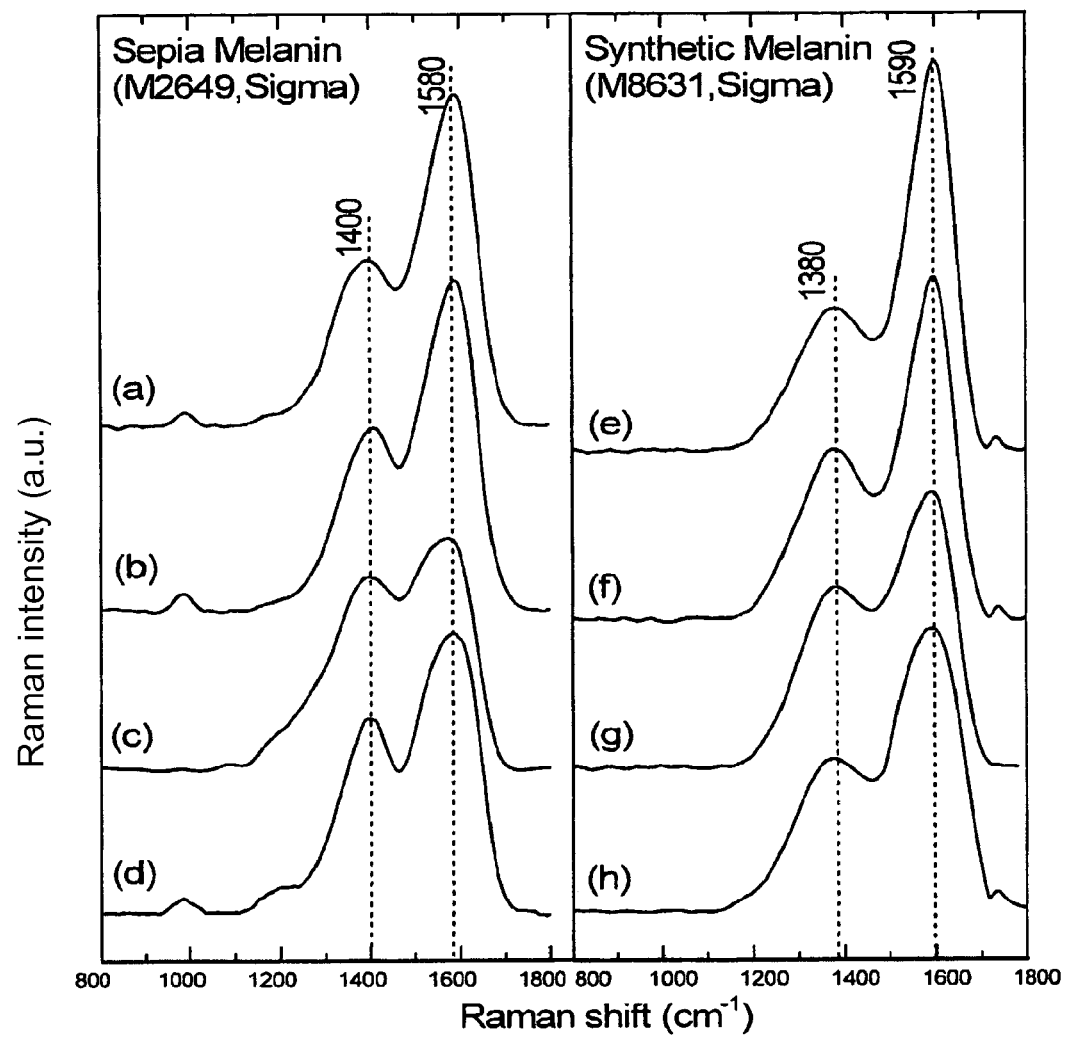
FIG. 14 shows Raman data for melanin.
Figure 14A:
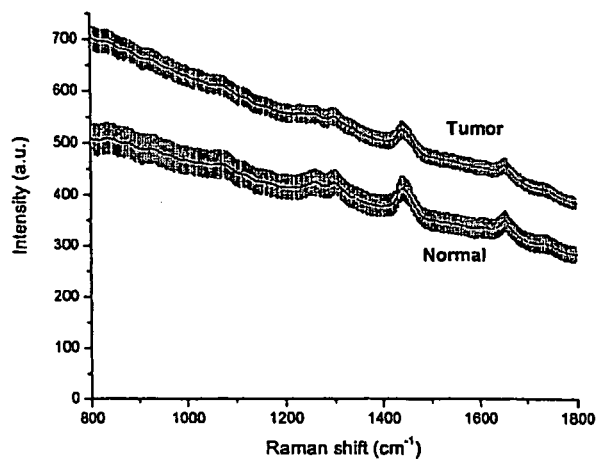
Figure 14B:
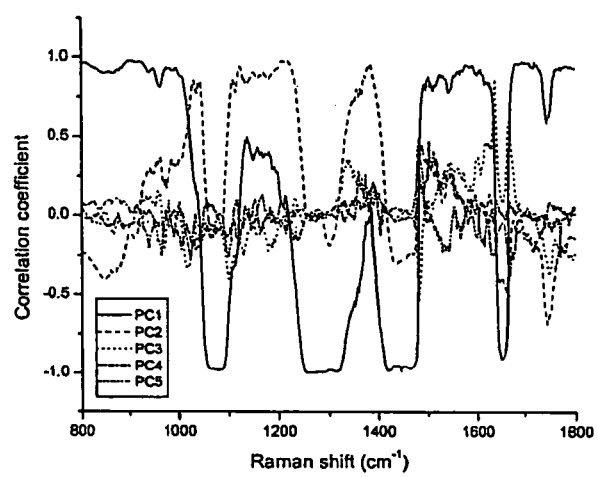
Figure 14C:
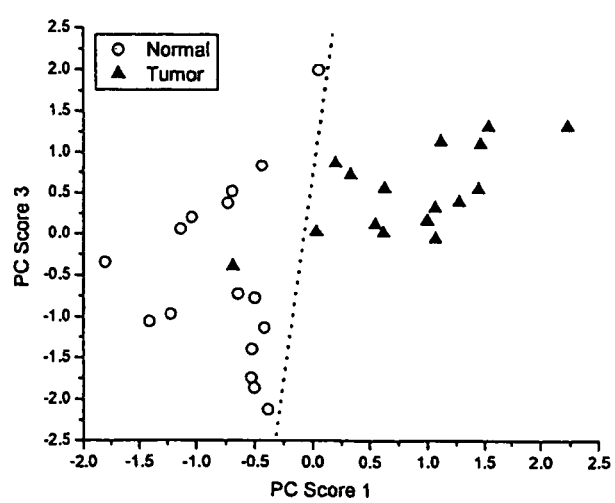

Curves 104, 105, and 106 of FIG. 11 are Raman spectra of tissues taken in vivo. These curves exhibit these peaks. FIG. 14 shows Raman data for melanin.

The spectra of cutaneous melanin-rich normal skin (curve 104) and pigmented lesions (curves 105 and 106) include two intense and broad bands peaking near 1368 $cm^{-1}$ and 1572 $cm^{-1}$ that are very similar to the Raman patterns observed in the melanin samples of FIG. 14. In addition, the in vivo skin Raman spectra exhibit vibrational bands for proteins and lipids that are different in various skin that appeared dark due to melanin. For instance, the weaker vibrational mode at 1742 $cm^{-1}$ which likely corresponds to C=O stretching of a lipid head group was present in highly pigmented skin lesions, while other bands were significantly reduced: e.g., the ν (C=O) amide I band at 1654 $cm^{-1}$, the δ ($CH_3$) and δ ($CH_2$) at scissoring mode at 1445 $cm^{-1}$, the $CH_2$ deformation at 1301 $cm^{-1}$, and the ν (CN) and δ (NH) amide III bands at 1269 $cm^{-1}$. The 1445 $cm^{-1}$ peak disappeared in the malignant melanoma spectrum but was observed in the benign compound nevus spectrum, whereas the converse was true for the 1269 $cm^{-1}$ peak. These differences as well as the peak positions and bandwidths of the two melanin Raman bands may be included as features and used for non-invasive melanoma detection in embodiments of the invention.

In some embodiments of the invention, the 1368 $cm^{-1}$ and/or 1572 $cm^{-1}$ melanin peaks are used directly or indirectly as an indicator of melanin concentration in a tissue specimen of interest. The melanin concentration may be used as a feature for tissue classification in addition to other features of the Raman and background fluorescence spectra. The magnitude of these peaks may be determined by subtracting the background. This may be achieved by fitting a function to the background. The fitting function should be a low order function such as a second-order polynomial since these peaks are so broad that a higher order fitting function will fit the peaks themselves.

Figure 17:
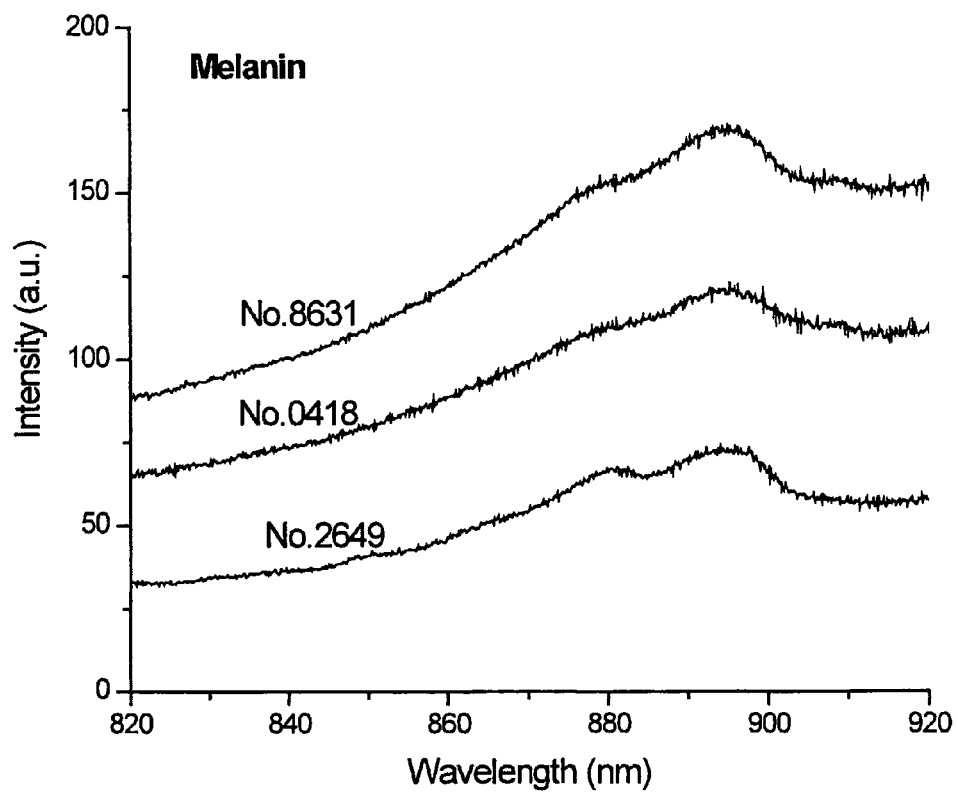
FIG. 17 shows NIR spectra for several melanin samples.

There is a relationship between melanin concentration and NIR background fluorescence. Although melanin fluoresces only weakly in the visible band, melanin fluoresces more strongly in the NIR wavelength range. Measurements on synthesized and extracted melanin products from Sigma confirm strong NIR fluorescence emission (see FIG. 17).

The 1368 $cm^{-1}$ and 1572 $cm^{-1}$ Raman bands may also be used independently in methods for measuring the melanin content of tissues. In such methods the intensities of one or both of these peaks is determined. This may be done, for example, by subtracting the background from the peaks as described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

methods according to the invention may optionally take into account features in addition to features of Raman spectra and background fluorescence spectra. For example, diffuse reflectance properties, ultraviolet or visible fluorescence properties could also be included in the analysis.

Any suitable mathematical techniques may be used to derive appropriate classification functions from reference data. Such techniques may include discriminant function analysis, logistic regression, multiple regression, or other suitable statistical analysis techniques.

While some of the examples given above relate to classifying skin, the invention is not limited to skin tissues but can equally be applied to other tissues including epithelial tissues of internal surface organs, such as the bronchial tree, the earns nose and throat, the gastrointestinal tract, the cervix, and the like. A fiber probe may be used with an endoscope to most easily obtain Raman and NIR background fluorescence spectra for internal tissues. A compact fiber probe suitable for obtaining Raman and NIR background fluorescence spectra through an endoscope is described in international patent application No. PCT/CA04/00062 entitled In vivo Raman endoscopic probe and methods of use and in corresponding U.S. patent application Ser. No. 10/761,703.

Instead of acquiring an essentially continuous spectrum containing Raman and background fluorescence features, the invention could be practiced by acquiring spectral information for a plurality of discrete wavelengths or for a plurality of wavelength ranges.

Accordingly, the scope of the invention is to be construed in accordance with the substance defined by the following claims.

What is claimed is:

1. A method for characterizing a tissue, the method comprising:
    obtaining features of a Raman spectrum of the tissue in a first wavelength range;
    obtaining features of a background fluorescence spectrum of the tissue in a second wavelength range overlapping with the first wavelength range, wherein the background fluorescence spectrum is a background to the Raman spectrum in the first wavelength range; and,
    characterizing the tissue based upon at least the Raman spectrum features and the background fluorescence spectrum features
    wherein the tissue is tissue of a subject and the method comprises:
    obtaining features of a Raman spectrum and a background fluorescence spectrum of a control area of normal tissue of the subject;
    wherein characterizing the tissue is based in part upon a difference between one or more features of the Raman spectrum of the tissue and the Raman spectrum of the control area and based in part on a difference between the background fluorescence spectrum of the tissue and the background fluorescence spectrum of the control area.

2. A method according to claim 1 wherein the first and second wavelength ranges include wavelengths in the near infrared.

3. A method according to claim 1 wherein the first and second wavelength ranges each include wavelengths from about 800 nm to about 1000 nm.

4. A method according to claim 1 wherein obtaining features of the background fluorescence spectrum and the Raman spectrum comprise illuminating the tissue with incident light that is substantially monochromatic and obtaining a raw spectrum by detecting light backscattered from the tissue at a plurality of infrared wavelengths.

5. A method according to claim 4 wherein characterizing the tissue comprises observing an intensity of the Raman spectrum at a Raman shift of 1445 $cm^{-1}$ relative to a wavelength of the incident light.

6. A method according to claim 4 wherein characterizing the tissue comprises observing an intensity of the Raman spectrum at a Raman shift of 1269 $cm^{-1}$ relative to a wavelength of the incident light.

7. A method according to claim 4 wherein characterizing the tissue comprises observing features within a band having a Raman shift in the range of about 1200 $cm^{-1}$ to about 1400 $cm^{-1}$ relative to a wavelength of the incident light.

8. A method according to claim 4 wherein characterizing the tissue comprises observing features within a band having a Raman shift in the range of about 1500 $cm^{-1}$ to about 1650 $cm^{-1}$ relative to a wavelength of the incident light.

9. A method according to claim 4 comprising:
    computing a melanin content of the tissue based upon intensities of the Raman spectrum at Raman shifts of approximately 1368 $cm^{-1}$ and 1572 $cm^{-1}$,
    wherein characterizing the tissue based upon at least the Raman spectrum features and the background fluorescence spectrum features comprises characterizing the tissue based upon at least the computed melanin content.

10. A method according to claim 1 wherein obtaining features of the background fluorescence spectrum comprises illuminating the tissue with infrared light and obtaining a raw spectrum by detecting light backscattered from the tissue at a plurality of infrared wavelengths.

11. A method according to claim 10 wherein obtaining features of the Raman spectrum comprises extracting the features of the Raman spectrum from the raw spectrum.

12. A method according to claim 11 wherein extracting the features of the Raman spectrum from the raw spectrum comprises fitting a background fitting function to the raw spectrum to yield a fitted background function and subtracting the fitted background function from the raw spectrum.

13. A method according to claim 12 wherein obtaining features of the background fluorescence spectrum comprises obtaining features of the fitted background function.

14. A method according to claim 10 wherein characterizing the tissue based upon at least the Raman spectrum features and the background fluorescence spectrum features comprises applying to the raw spectrum a classification function derived from principal components analysis.

15. A method according to claim 1 wherein characterizing the tissue based upon at least the Raman spectrum features and the background fluorescence spectrum features comprises applying to one or more datasets a classification function derived from principal components analysis, the one or more datasets collectively including the Raman spectrum features and the background fluorescence spectrum features.

16. A method according to claim 15 wherein the one or more datasets include one or more Raman spectrum principal component scores and one or more background fluorescence spectrum principal component scores.

17. A method according to claim 15 wherein applying the classification function comprises applying a predetermined principal component to data of the one or more datasets.

18. A method according to claim 15 wherein the tissue is skin of a part of a subject's body and the method comprises selecting a classification function corresponding to the part of the subject's body from a plurality of classification functions each corresponding to a different body region.

19. A method according to claim 18 wherein the plurality of classification functions includes classification functions corresponding to two or more of the following body parts: head, torso, hand, and arm or thigh.

20. A method according to claim 1 wherein characterizing the tissue comprises applying the Raman spectrum features and the background fluorescence spectrum features as inputs to a neural network.

21. A method according to claim 1 where the tissue is a section of skin.

22. A method according to claim 1 wherein the tissue comprises lung tissue.

23. A method according to claim 1 wherein the tissue comprises epithelial tissue.

24. A method according to claim 23 wherein the epithelial tissue comprises tissue lining the subject's gastrointestinal tract.

25. A method according to claim 23 wherein the epithelial tissue comprises a lining of the subject's ear, nose or throat.

26. A method according to claim 1 wherein the method is applied to screening for skin cancer.

27. A method according to claim 1 wherein the method is applied to screening for one or more conditions selected from the group consisting of: basal cell carcinoma, squamous cell carcinoma, melanoma, actinic keratosis, seborrheic keratosis, sebaceous hyperplasia, keratoacanthoma, lentigo, melanocytic nevi, dysplastic nevi, and blue nevi.

28. A method according to claim 1 wherein characterizing the tissue comprises observing one or both of: an intensity of the Raman spectrum at a Raman shift of 1445 $cm^{y1}$ relative to a wavelength of the incident light and an intensity of the Raman spectrum at a Raman shift of 1269 $cm^{-1}$ relative to a wavelength of the incident light and wherein characterizing the tissue comprises indicating whether the tissue is likely affected by melanoma.

29. A method according to claim 1 wherein characterizing the tissue comprises observing one or both of: an intensity of the Raman spectrum at a Raman shift of 1445 $cm^{-1}$ relative to a wavelength of the incident light and an intensity of the Raman spectrum at a Raman shift of 1269 $cm^{-1}$ relative to a wavelength of the incident light and wherein characterizing the tissue comprises indicating whether the tissue is likely compound nevus tissue.

30. A method according to claim 1 wherein the features of the Raman and fluorescence spectra are acquired with the tissue in vivo.

31. A method according to claim 30 wherein the tissue is located below a tissue surface and acquiring the features of the Raman and fluorescence spectra comprises detecting light from the tissue after the light has passed through overlying tissue.

32. Apparatus for characterizing tissues, the apparatus comprising:
a light source for illuminating a section of tissue;
an optical system configured to collect and direct backscattered light from the section of tissue into a spectrometer, the backscattered light comprising background fluorescence and Raman scattered light;
a data processor connected to receive spectrum information for the backscattered light from the spectrometer, the spectrum information including information about features of a Raman spectrum of the section of tissue in a first wavelength range of the backscattered light and information about features of a background fluorescence spectrum of the section of tissue in a second wavelength range of the backscattered light, the second wavelength range overlapping with the first wavelength range, wherein the background fluorescence spectrum is a background to the Raman spectrum in the first wavelength range;
wherein the data processor is configured to characterize the section of tissue based upon at least the Raman features and the background fluorescence features of the section of tissue and the characterizing of the section of tissue by the data processor is:
based in part on a difference between one or more features of the Raman spectrum of the tissue and a Raman spectrum of a control area of normal tissue; and
based in part on a difference between the background fluorescence spectrum of the tissue and a background fluorescence spectrum of the control area.

33. Apparatus according to claim 32 comprising at least one classification function accessible to the data processor, the classification function producing a classification result in response to an input, the input including information about at least one Raman feature and at least one background fluorescence feature of a spectrum of a tissue;
wherein the data processor is configured to apply the classification function to the spectrum information to obtain a corresponding classification result and to generate an output based upon the corresponding classification result, the output indicative of whether the section of tissue is likely to include abnormal tissue.

34. Apparatus according to claim 33 comprising a plurality of classification functions and a mechanism for permitting a user to select an appropriate one of the classification functions.

* * * * *

UNITED STATES PATENT AND TRADEMARK OFFICE
CERTIFICATE OF CORRECTION

| | | |
|---|---|---|
| PATENT NO. | : 8,326,404 B2 | Page 1 of 1 |
| APPLICATION NO. | : 10/596072 | |
| DATED | : December 4, 2012 | |
| INVENTOR(S) | : Haishan Zeng et al. | |

It is certified that error appears in the above-identified patent and that said Letters Patent is hereby corrected as shown below:

On the Title page, Item [75], the residence of inventor Harvey Lui, appearing as "Singapore (SG)", is changed to --Vancouver (CA)--

Signed and Sealed this
Fifth Day of March, 2013

Teresa Stanek Rea
*Acting Director of the United States Patent and Trademark Office*